US008741329B2

(12) United States Patent
de Graaff et al.

(10) Patent No.: US 8,741,329 B2
(45) Date of Patent: Jun. 3, 2014

(54) DRUG DELIVERY SYSTEM

(75) Inventors: Wouter de Graaff, Oss (NL); Raymond Zeeman, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 249 days.

(21) Appl. No.: 12/234,261

(22) Filed: Sep. 19, 2008

(65) Prior Publication Data

US 2009/0081278 A1    Mar. 26, 2009

(30) Foreign Application Priority Data

Sep. 21, 2007    (EP) ..................................... 07018584

(51) Int. Cl.
*A61F 6/14*    (2006.01)
*A61K 9/00*    (2006.01)
*A61K 31/56*    (2006.01)
*A61F 2/04*    (2013.01)

(52) U.S. Cl.
USPC ............ 424/430; 424/400; 424/422; 514/170

(58) Field of Classification Search
None
See application file for complete search history.

(56) References Cited

U.S. PATENT DOCUMENTS

| | | | |
|---|---|---|---|
| 3,545,439 A | 12/1970 | Duncan | |
| 3,854,480 A * | 12/1974 | Zaffaroni | ...................... 424/424 |
| 3,995,633 A | 12/1976 | Gougeon | |
| 3,995,634 A | 12/1976 | Drobish | |
| 4,237,885 A | 12/1980 | Wong et al. | |
| 4,292,965 A | 10/1981 | Nash et al. | |
| 4,596,576 A | 6/1986 | De Nijs | |
| 4,629,449 A | 12/1986 | Wong | |
| 5,840,771 A | 11/1998 | Oldham et al. | |
| 5,851,547 A | 12/1998 | Fujioka et al. | |
| 5,972,372 A * | 10/1999 | Saleh et al. | ................... 424/432 |
| 5,989,581 A | 11/1999 | Groenewegen | |
| 6,579,533 B1 | 6/2003 | Tormala et al. | |
| 6,590,081 B1 * | 7/2003 | Zhang | ........................... 530/399 |
| 6,831,073 B1 | 12/2004 | Lanquetin et al. | |
| 6,906,049 B1 | 6/2005 | Paris et al. | |
| 7,749,987 B2 | 7/2010 | Paris et al. | |
| 2003/0007992 A1 | 1/2003 | Gibson et al. | |
| 2003/0059456 A1 | 3/2003 | Malcolm et al. | |
| 2004/0062804 A1 | 4/2004 | Lee et al. | |
| 2006/0252835 A1* | 11/2006 | Broquaire et al. | ............ 514/618 |
| 2006/0280771 A1 | 12/2006 | Groenewegen et al. | |
| 2008/0242650 A1 | 10/2008 | Thomas | |

FOREIGN PATENT DOCUMENTS

| | | | |
|---|---|---|---|
| EP | 0 050 867 | | 1/1988 |
| EP | 0 303 306 | | 3/1993 |
| EP | 0 659 406 | B1 | 3/2000 |
| EP | 1 084 703 | A1 | 3/2001 |
| EP | 0 876 815 | | 1/2002 |
| WO | 89/09066 | A1 | 10/1989 |
| WO | WO97/02015 | | 1/1997 |
| WO | WO99/30976 | | 6/1999 |
| WO | 03/017971 | A1 | 3/2003 |
| WO | WO/2004/103336 | * | 5/2004 ............. A61K 45/06 |
| WO | WO2005/004837 | | 1/2005 |
| WO | WO2005/089723 | | 9/2005 |
| WO | WO2007/001888 | | 1/2007 |
| WO | 2009/035562 | A2 | 3/2009 |

OTHER PUBLICATIONS

Nascimento et al. "Nomegestrol acetate contraceptive implant use by women with sickle cell disease". Clin Pharmacol Ther. Oct. 1998; 64(4) abstract.*
Davies et al, "Ovarian Activity and Bleeding Patterns During Extended Continuous use of a Combined Contraceptive Vaginal Ring", Contraception, 1992, 269-278, 46, Butterworth-Heinemann.
Davies et al, "The Effects of a Combined Contraceptive Vaginal Ring Releaseing Ethinyloestradiol and 3-Ketodesogestrel on Vaginal Flora", Contraception, 1992, 511-518, 45, Butterworth-Heinemann.
Keskar et al, "Cervical cancer treatment with a locally insertable controlled release delivery system", Journal of Controlled Release, 2006, 280-288, (115), Elsevier Science.
Kim et al, "Application of Binary Polymer System in Drug Release Rate Modulation. 2. Influence of Formulation Variables and Hydrodynamic Conditions on Release Kinetics", Journal of Pharmaceutical Sciences, 1997, 323-328, 86(3).
Kubba et al, "Contraception", The Lancet, 2000, 1913-1919, (356).
Laarhoven et al, "In vitro release properties of etonogestrel and ethinyl estradiol from a contraceptive vaginal ring", International Journal of Pharmaceutics, 2002, 163-173, 232, Elsevier Science.
Ladipo et al, "Contraceptive implants", Current Opinion in Obstetrics and Gynecology, 1994, (6)564-569.
Malcolm et al, "In vitro release of nonoxynol-9 from silicone matrix intravaginal rings", Journal of Controlled Release, 2003, 355-364, (91), Elsevier Science.
Pellett-Madan et al, "Prioritizing prevention of HIV and sexually transmitted infectons: first-generation vaginal microbicides", Current Opinion in Infectious Diseases, 2006, 49-54, (19).
Nascimento et al, "Nomegestrol acetate contraceptive implant use by women with sickle cell disease", Clinical Pharmacology and Therapeutics, 1998, 433-438, 64(4), Mosby, Inc.
Woolfson et al, "Design of an intravaginal ring for the controlled delivery of 17β-estradio as its 3-acetate ester", Journal of Controlled Release, 1999, 319-328, (61), Elsevier Science.
Woolfson et al, "Design of an silicone reservoir intravaginal ring for the delivery of oxybutynin", Journal of Controlled Release, 2003, 465-476, (91), Elsevier Science.

(Continued)

*Primary Examiner* — Robert A Wax
*Assistant Examiner* — Danah Al-Awadi
(74) *Attorney, Agent, or Firm* — Janet E. Fair; Anna L. Cocuzzo

(57) ABSTRACT

The subject invention provides a drug delivery system comprising at least one compartment comprising (i) a drug-loaded thermoplastic polymer core layer, (ii) a drug-loaded thermoplastic polymer intermediate layer and (iii) a non-medicated thermoplastic polymer skin covering the intermediate layer, wherein said core layer is loaded with crystals of a first (pharmaceutically) active compound and said intermediate layer is loaded with, crystals of the second (pharmaceutically) active compound.

34 Claims, 28 Drawing Sheets

(56) References Cited

OTHER PUBLICATIONS

Zaneveld et al, Use of mandelic acid condensation polymer (SAMMA), a new antimicrobial contraceptive agent, for vaginal prophylaxis, Fertility and Sterility, 2002, 78(5), 1107-1115.
Written Opinion of International Patent Application PCT/EP2008/007975 dated Mar. 21, 2010.
Office Action dated Apr. 28, 2010 in U.S. Appl. No. 10/558,040.
"Silastic", retrieved from "http://en.wikipedia.org/wiki/Silastic", downloaded Dec. 21, 2010.
"Thermoplastic", retrieved from "http://en.wikipedia.org/wiki/Thermoplastic", downloaded Dec. 21, 2010.
"Thermoset polymer matrices", retrieved from "http://en.wikipedia.org/wiki/Thermoset_polymer_matrices", downloaded Dec. 21, 2010.

* cited by examiner

US 8,741,329 B2

DRUG DELIVERY SYSTEM

FIELD OF THE INVENTION

The present invention relates to the field of medicine, in particular reproductive medicine such as female contraception, hormone replacement therapy, regulation of ovarian function and so forth.

The present invention relates to a drug delivery system (device) for the simultaneous release of two or more active substances, which system releases the active substances in a substantially constant ratio over a prolonged period of time. The drug delivery system can be in different forms, such as an implant, an intrauterine system (IUS), a helical coil, a spring and is in particular a ring-shaped vaginal drug delivery system. When the invention pertains to a drug delivery article for intra-vaginal use, its use is focused on typically female medical indications, such as contraception and hormone-replacement therapy. In one embodiment, the article according to the invention is particularly in the form of a ring, which will hereinafter be referred to as a vaginal ring.

BACKGROUND OF THE INVENTION

Vaginal rings are known. Background art in this respect includes the following patent documents.

U.S. Pat. Nos. 3,995,633 and 3,995,634, describe separate, preferably spherical or cylindrical, reservoirs containing different active substances, which are assembled in specially constructed holders.

U.S. Pat. No. 4,237,885 describes a tube or coil of polymeric material which is divided into portions by means of a plurality of "spacers" provided in the tube, after which each of the separate tube portions is filled with a different active substance in a silicone fluid and the two ends of the tube are subsequently connected to one another. In this release system, however, transport (diffusion) of active material from one reservoir to the other takes place through the wall of the tube, especially upon prolonged storage, so that the pre-set fixed release ratio between the active substances in question will change over time.

European patent publication 0,050,867 discloses a two-layered vaginal ring which comprises a pharmacologically acceptable supporting ring covered by two layers preferably of silicone elastomers whereby the inner layer is a silicone elastomer loaded with an active substance.

U.S. Pat. No. 4,292,965 describes a ring shaped vaginal delivery system of three layers made of silicone elastomers.

U.S. Pat. No. 4,596,576 describes a two-compartment vaginal ring wherein each compartment contains a different active substance. To achieve a suitable ring with a constant release ratio between the various active substances, the end portions of the compartments are joined by glass stoppers.

Patent Publication WO 97/02015 describes a two-compartment device, a first compartment consisting of a core, a medicated middle layer and a non medicated outer layer, and a second compartment consisting of a medicated core and a non medicated outer layer.

EP 876 815 discloses a vaginal ring (Nuvaring®) which is designed for the simultaneous release of a progestogenic steroid compound and an estrogenic steroid compound in a fixed physiological ratio over a prolonged period of time. The drug delivery system comprises one compartment comprising a thermoplastic polymer core containing the mixture of the progestogenic and estrogenic compounds and a thermoplastic polymer skin, the progestogenic compound being initially dissolved in the polymer core material in a relatively low degree of supersaturation.

Patent Publication WO2004/103336 describes a drug delivery system comprising at least one compartment consisting of a drug-loaded thermoplastic polymer core, a drug-loaded thermoplastic polymer intermediate layer and a non-medicated thermoplastic polymer skin covering the intermediate layer. The intermediate layer is loaded with crystals of a progestogenic compound and with estrogenic compound in a dissolved form. The core is loaded with the estrogenic compound in a dissolved form.

Patent publication WO2005/089723 discloses a ring with one or more compartments in which one compartment comprises a core in which a progestogenic compound is dissolved up to a concentration below the saturation level at 25° C. The core also comprises an estrogenic compound. The compartment furthermore comprises a skin that is permeable for both the progestogenic and estrogenic compound.

From the above disclosures, it is clear that e.g. the material, the layers and the compartments are all aspects which play a role in the development of a ring device.

All choices are usually made with a view to obtain a constant release pattern, which is complicated when two or more active substances are involved. The latter is of particular importance in the field of contraception, as for this purpose often a combination of a progestogen and an estrogen is used, the release pattern of which must result in a contraceptive effect. Also in hormone replacement therapy, it may be desired to have rings, which deliver combinations of drugs.

Among the above disclosures, EP 876 815, WO2005/089723 and WO2004/103336 clearly set a standard; they involve one-compartment ring designs, they obviate the need for silastic polymer by using ethylene vinyl acetate (EVA) combinations, and they release two or more active substances in a substantially constant ratio to one another over a prolonged period of time.

As any product of technology at all times however, also the latter can still be improved upon. The drug delivery devices described in EP 876 815, WO2005/089723 and WO 2004/103336 require that all active compounds are present in the dissolved state (EP 876 815 and WO2005/089723) or that all compounds except for one (WO 2004/103336) are present in the dissolved state. This prerequisite severely limits the amount of drug that can be loaded into the polymeric matrix. An increase of the drugs concentration above a certain critical threshold value (J. van Laarhoven et al, Journal of Controlled Release, 82, 2002, p 309-317) will inevitably result in crystallization of the drug in the polymeric matrix. Consequently, the drug delivery systems disclosed in both EP 876 815, WO2005/089723 and WO 2004/103336 are not suitable when using two pharmaceutically active compounds which are both present in a solid state. This may happen when the active compounds have a relatively poor solubility in the polymers used, such as EVA polymers, and/or require a relatively high drug load in the polymeric matrix in order to obtain the required release pattern. When both drug substances are present in the crystalline form, the dissolved concentration of both compounds is per definition the saturation concentration of each compound. Consequently, it is not possible to adjust the release rate of one of such pharmaceutically active compounds independently from the other, by varying the concentration of the active compounds as their concentration will remain equal to their saturation concentration. Variation of the skin thickness will also not contribute to the adjustment of the release rate of one of such pharmaceutically active compounds independently from the other because an increase or a decrease of the skin thickness will influence the release of both compounds in the same direction.

It is therefore the object of the present invention to provide a drug delivery system in which the release rate of the two compounds that are partly present in the solid state and partly in the dissolved state can be regulated independently from one another.

SUMMARY OF THE INVENTION

This problem is solved by the invention by a drug delivery system comprising at least one compartment, which comprises (i) a drug-loaded thermoplastic polymer core layer, (ii) a drug-loaded thermoplastic polymer intermediate layer and (iii) a non-medicated thermoplastic polymer skin covering the intermediate layer, wherein said core layer is loaded with crystals of a first compound, in particular a pharmaceutically active compound, and wherein said intermediate layer is loaded with crystals of a second compound, in particular a pharmaceutically active compound.

In a first embodiment of the invention the core layer forms the core of the drug delivery system. In an alternative embodiment, the drug delivery system comprises an additional non-medicated core that is covered by the core layer.

The drug delivery system according to the invention may also comprise more layers than the core, intermediate and skin layers mentioned above. The layers form a tri- or multi-axial fiber that is used for shaping a delivery system. The delivery system may have the form of a ring, an implant, an intrauterine system (IUS), a helical coil or a spring.

The drug delivery system of the invention is preferably a single compartment system, which means that the whole system consists of the same segment that is made of the same type of drug loaded reservoir e.g. a fiber. The fiber can consist of three, four or more layers, of which at least two layers are loaded with an active ingredient in crystalline form.

The subject drug delivery system thus solves the above problem since it allows to adjust, independently from one another, the release rate of two active compounds, in particular pharmaceutically active compounds, that are present in the crystalline state in the polymer, for example because they have a relatively poor solubility in EVA polymers and/or require a relatively high drug load in the polymeric matrix in order to obtain the desired release profile.

The present invention relates to a drug delivery system formed from a fiber that consists of at least three co-axial layers. The outer layer is non-medicated but at least two of the inner layers are loaded with a drug that is in crystalline form.

FIG. 14 illustrates an embodiment of the invention in which the drug delivery system is comprised of three layers of which the core and intermediate shell are loaded with the active compounds A and B, respectively. The active compounds ("actives A and B") are both loaded above their respective saturation concentration and both are partly present in the crystalline state.

Immediately after manufacturing of the delivery system internal diffusion will start resulting in re-distribution of the active compounds. A fraction of the actives A and B will dissolve in the polymer until the saturation concentration is reached and simultaneous internal diffusion will level out the internal concentration gradient. The diffusion process resulting in leveling of internal concentration differences is visualized for active A in FIG. 15. The time point t∞ corresponds with the moment the system reaches equilibrium.

The fraction of the actives A and B that is present in the crystalline state, however, will not diffuse and hence not re-distribute in the system. Therefore, the crystals of the actives A and B will remain in the core and intermediate shell where they were initially loaded during manufacturing. This spatial separation of the crystals of the actives A and B results in a distinct diffusion path for these compounds which is illustrated in FIG. 16. When the drug delivery device is inserted in a medium—either in vitro or in vivo—external diffusion immediately will start to take place. In a transient phase the dissolved part of the compounds A and B, close to the surface of the device, will diffuse out of the system very rapidly resulting in an initial burst. Simultaneously, an internal concentration gradient starts to develop and the steady state situation is illustrated in FIG. 16.

Without being bound by theory it is anticipated that during release the concentration of active A in the core will remain equal or very close to the saturation concentration. External diffusion out of the core will result in a local decrease of the concentration in the core, which results in a driving force for the crystals dispersed throughout the core to dissolve in the polymer matrix. Thus, the decrease of the concentration of dissolved active A due to diffusion is readily counterbalanced by crystals going into dissolution and a concentration gradient will develop over both the intermediate and skin.

Based on analogous arguments it is anticipated that active B will develop a concentration gradient only over the skin. Consequently in steady state the diffusion length for active A and active B are distinct and variation in the dimensions and/or composition of skin and intermediate layer will provide a means to tune the absolute release rate as well as the ratio in which the actives A and B are released by the system.

The subject invention thus provides a three-layer design drug delivery system from which two active compounds; in particular pharmaceutically active compounds, can be released independently from one another. The invention is particularly useful for simultaneous release of two pharmaceutically active compounds that have a relatively poor solubility in thermoplastic polymers (such as EVA polymers) and require a relatively high load in the polymeric matrix in order to obtain the desired release pattern, thus inevitably being present in their solid (crystalline) form in the polymer matrix.

Another object of the subject invention is to increase the efficiency of the drug substances employed in the drug delivery system and to minimize the remnant drug content in the used system.

By another of its aspects the present invention provides a method of contraception that makes use of the drug delivery system of the invention, in particular the vaginal ring.

By yet another of its aspects the present invention provides a method of hormone replacement therapy that makes use of the drug delivery system of the invention, in particular the vaginal ring.

In accordance with another embodiment, there is provided a method of concomitantly providing contraception and treating or preventing a sexually transmitted disease.

Also provided, by another aspect of the invention, is a method of manufacturing the three-layered drug delivery system of the invention.

DETAILED DESCRIPTION OF THE INVENTION

Figure 1A:
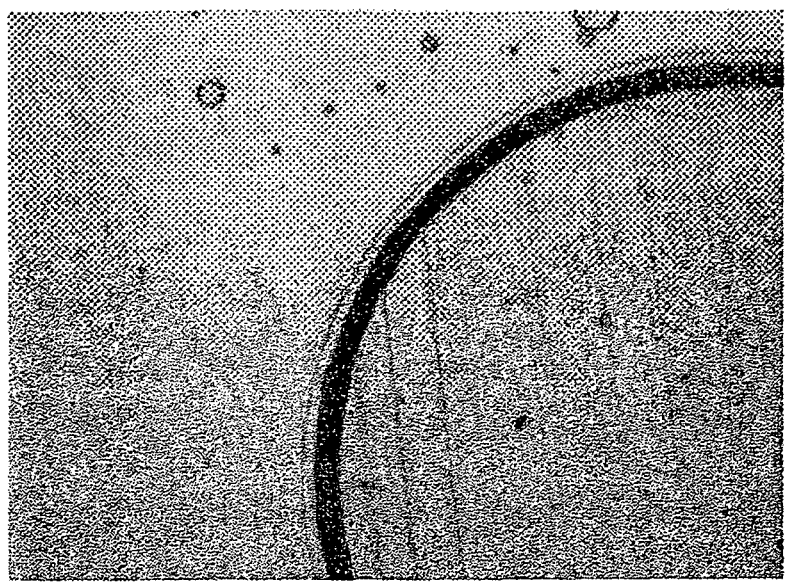
FIGS. 1A, 1B and 1C show a cross-section of a three-layered fiber of variant A, B and C, respectively, as described in the examples.

The subject invention provides a drug delivery system comprising at least one compartment consisting of three-layers: (i) a polymer based core layer, (ii) a polymer based intermediate layer and (iii) a polymer based skin covering the intermediate layer, wherein said core layer comprises crystals of the first pharmaceutical compound (drug or active) and wherein said polymer intermediate layer comprises crystals of the second pharmaceutical compound.

In a first embodiment of the invention the core layer forms the core of the drug delivery system. In an alternative embodiment, the drug delivery system comprises an additional non-medicated core that is covered by the core layer.

Thus during manufacturing the drug crystals are not dispersed in a single layer, but crystals of the actives A and B are dispersed in two separated layers. A fraction of the actives A and B will dissolve in the polymer until the saturation concentration is reached and simultaneous internal diffusion will level out the internal concentration gradients. The crystals of the active compounds A and B are immobile and hence the crystals of the actives A and B stay spatially separated in the layers in which they were initially loaded.

The release kinetics of a drug delivery system intended for the simultaneous release of two active compounds is characterized by two essential attributes; the absolute rate in which the two compounds are released from the delivery system and the mutual ratio in which these compounds are released. The absolute release rate of the actives A and B from the delivery system can be tuned by adjusting the skin thickness. The ratio, in which these compounds are released, however, will remain essentially unaffected by skin thickness variations, because adjustment of the skin thickness affects the diffusion path of the compounds A and B equally.

Known solutions (EP 876 815, WO2005/089723 and WO2004/103336) for independent release tuning of two compounds from the same compartment are not suitable, since these solutions are based on the attribute that at least one compound is entirely dissolved in the delivery system. Obviously this is not the case for a system according to the object invention containing two actives both partly present in crystalline form. For this reason a new and alternative mechanism for adjusting the mutual release ratio had to be contemplated.

In the new concept independent adjustment of the release of two actives from the same compartment is achieved by the creation of a distinct diffusion path for the actives A and B. For this purpose A and B are loaded in the same compartment in two separate layers. In a delivery system with crystals of the active compounds A and B loaded in the core layer and intermediate layer respectively, compound A will develop a concentration gradient over both the intermediate layer and skin, while active B will develop a concentration gradient only over the skin. The different diffusion length of the compounds A and B provide a means to independently adjust the ratio in which these compounds are released from the system.

The diffusion length of the compound loaded in the core layer can be adjusted by varying the thickness of the intermediate layer. Thus by varying the intermediate layer thickness the release rate of the compound loaded in the core layer can be tuned up or down, by decreasing or increasing intermediate layer thickness. The diffusion path of the compound loaded in the intermediate layer, however, remains essentially unchanged and hence the release rate also remains essentially unaffected. Thus, the release rate of the drug compound loaded in the core layer can be changed without affecting the release rate of the drug compound loaded in the intermediate layer and hence the release ratio can be adjusted towards the desired ratio. Once the desired release ratio is obtained, the absolute release rate can be adjusted by choosing the right skin thickness.

Another possibility to change the release ratio drastically is to reverse the drug load in the core layer and intermediate layer. Instead of loading active A in the core layer and B in the intermediate layer, B can be loaded in the core layer and A in the intermediate layer. A further means to tune the release ratio is to make use of different polymer grades used for the intermediate layer.

The diffusion path of the drug loaded in the core layer leads through the intermediate layer and skin. The composition of the intermediate layer, however, is not constant. During use or in-vitro release testing the size and concentration of solid particles loaded in the intermediate layer will gradually decrease to a fraction of the initial content and particle size. Surprisingly it was found that the release rate of the drug compound loaded in the core—which diffuses through a layer of variable composition—is not largely affected and remains essentially zero order.

Another object of invention is an increased efficiency of the drug delivery system, which means a lower residual drug content in the system after use. The remnant content after use of both drug A and drug B in the delivery system of the invention, can be restricted to less ten 20-40 wt % of the declared amounts. This is a very considerable improvement compared to prior art delivery system containing drugs solely in dissolved form (EP 876 815, NuvaRing® and WO2005/089723) or systems which contain at least one entirely dissolved active (WO2004/103336). For instance, the remnant drug content after use in NuvaRing® is about 78 wt % and 88 wt % for etonogestrel and ethinyl estradiol, respectively. For three layered rings as described in WO2004/103336 the drug substance efficiency of the (entirely) dissolved compounds is not improved compared to NuvaRing®.

Without being bound by theory the improved efficiency of the delivery system according to the object invention can be understood in terms of a stabilized concentration gradient in the delivery system. The new delivery system contains crystals of both compounds and hence a decrease of the dissolved concentration of both drugs due to diffusion out of the system will be counterbalanced by crystals going into dissolution. This means that the concentration gradient during (semi) steady state release remains essentially constant as long as the dissolution rate of the crystals is in conjunction with the drug transport out of the system.

The essence of this novel three-layered drug delivery system of the subject invention lies in the provision of the possibility to adjust the release rates of two pharmaceutically active compounds independently from one another in spite of the fact that the compounds used in the subject invention are both present in their solid (crystalline) state in the polymer matrix because they have a relatively poor solubility in thermoplastic polymers and/or require a relatively high load in the polymeric matrix in order to obtain the desired release ratio and/or release rate, thus inevitably being present in the crystalline state.

The fibre can consist of three layers but may also comprise one or more additional layers. An example of an additional layer can be an non-medicated core that is covered by the medicated core layer. An non-medicated core can be advantageous for the efficiency of the drug delivery system. The core mainly acts to give the fibre its predetermined thickness, which means that the core comprises a large volume. A large core reservoir (in a three-layer design) should contain the drug substance in such a level that crystalline material is and remains present. This could mean that a large excess of drug substance is needed. In case an additional non-medicated core (fourth layer) is present, the inner medicated layer must contain the drug substance at a higher concentration, without effecting the release rates. Due to this higher concentration, the average diffusion path is shorter and the release rate might be even more constant. A higher drug substance efficiency can thus be achieved without influencing the release profiles significantly.

In another embodiment, additional layers may be comprised between the medicated layers. This can be used as a further means to differentiate the diffusion path for the compound loaded in core-layer and intermediate shell.

According to the invention, various other configurations are possible provided that at least two layers are medicated and that the active compounds in these layers are at least partially present in the solid state.

A drug delivery system of the subject invention can be used in any mammal, in particular a female mammal. In a specific embodiment, the mammal is a human female.

The drug delivery system of the invention can be provided in various forms that are made from the multi- or three-layered fiber that comprises a medicated core layer, a medicated intermediate layer and a non-medicated skin. The core layer may be the core or may cover a non-medicated core. Suitable forms comprise substantially ring-shaped forms, rods, T-shapes etc.

The term "substantially ring-shaped form" should be understood to encompass in addition to ring shaped devices any other essentially ring-shaped structures that are appropriate for vaginal administration, such as for example helically coiled spirals and ring devices having convoluted surface. Implants have usually a rod-shaped form, whereas intra-uterine systems are normally T-shaped.

The desired release ratio depends on the indication sought to be used with the drug delivery device of the subject invention, such as, but not limited to, contraception or hormone replacement therapy.

The provision of a fiber as used in a drug delivery system of the subject invention is accomplished by (1) loading the core of the fiber with a first (pharmaceutically) active compound in solid (crystalline) form and (2) loading the intermediate layer of the fiber with a second pharmaceutically active compound in solid form, thereby providing a fiber wherein both compounds are physically separated and present in their solid form in two distinct layers, i.e. the core and the intermediate layer. The dissolved part of both pharmaceutically active compounds is present all over the fiber in all layers once equilibrium is reached. The solid part of both drug substances remains separated.

In a specific embodiment of the subject invention, the (pharmaceutically) active compounds have a relatively poor solubility in thermoplastic polymers such as EVA polymers and require a relatively high load in the polymeric matrix in order to obtain the desired release ratio. In a more specific embodiment of the invention, both pharmaceutically active compounds are steroids.

However, the invention can as be used to release other active compounds that need to be administered concomitantly and in a particular ratio As an example of a preferred embodiment of the invention the following passages refer to vaginal rings and steroids, although non-steroidal compounds and other forms of the drug delivery system are contemplated by the subject invention as well.

The release of steroids from the ring is influenced by the solubility and diffusion coefficient of the steroid in the polymer. In a specific case of steroids that have a relatively poor solubility in the polymer matrix and which require a relatively high load in the polymeric matrix in order to obtain the desired release pattern, the steroids will be incorporated into the matrix in their solid form and will be dissolved in the polymeric matrix until saturation is reached. In such a system the dissolved concentration cannot be chosen freely, but is equal to the saturation concentration.

Consequently, the steroid load cannot be used to tune the release to the desired rate, because varying the steroid load will not result in a higher or lower dissolved steroid concentration, as the steroid concentration will remain equal to the saturation concentration. Variation of the skin thickness will have a limited contribution to the adjustment of the release rate of more than one of such pharmaceutically active compound independently from one another because an increase or a decrease of the skin thickness will in general influence the release of both compounds in the same direction.

After the ring has been put in a sink, steroid will start to diffuse out of the ring and the concentration of the steroid dissolved in the polymeric matrix will drop slightly. As a consequence thereof, the solid steroid will start to dissolve. Thus, the decrease of the concentration gradient due to diffusive transport out of the ring is counterbalanced by the dissolution of the steroid present in a solid form.

Hence, the concept of the three-layer vaginal ring of the invention is to load: (1) the core with a first steroid (A) that has a relatively poor solubility in EVA polymers and requires a relatively high load in the polymeric matrix in order to achieve the desired release profile; and to load (2) the intermediate layer with a second steroid (B) that has a relatively poor solubility in EVA polymers and requires a relatively high load in the polymeric matrix in order to achieve the desired release profile. Thus, both compound A and compound B are present in the polymer matrix in a solid state.

As will be appreciated, the desired release rates of steroid A and steroid B are obtained by separately placing the compounds in two distinct layers. The release rates may further be adjusted by varying the thickness and/or by varying the grade of the EVA polymer intermediate layer.

The three-layer vaginal ring of the invention can be designed to afford different ratios between the average release rates of compound A and compound B. The ratio between the average release rates of the steroidal compounds may be influenced by varying the location of the compounds, i.e. by loading compound A in the core and compound B in the intermediate layer or vice versa. The release ratio can be further adjusted by varying the intermediate layer thickness and/or by varying the intermediate layer polymer grade.

Further, the optimization of a ring intended for the simultaneous release of two compounds towards certain pre-set release specifications, requires the possibility to adjust both the relative ratio in which two drug compounds (A and B) are released as well as the possibility to tune the absolute rate in which the compounds are released daily.

If on the other hand, both steroids with relatively low solubility in the polymer matrix were loaded relatively high, together, in one single layer (i.e. in the intermediate layer or in the core), consequently both being present in their solid (crystalline) state, the release rate would be mainly governed by the solubility and diffusivity of the steroids in the polymer matrix. In such a case, only by shear coincidence would the desired release ratio be obtained.

The vaginal ring of the subject invention can be manufactured by the known process of extrusion, such as co-extrusion and/or blend-extrusion. The drug-loaded-core, the drug-loaded intermediate layer and the non-medicated outer layer are all co-extruded. The fibers thus obtained are cut into pieces of the required length and each piece is assembled to a ring-shaped device in any suitable manner. The rings are then packed for example in a suitable sachet, optionally after being sterilized or disinfected.

The vaginal ring of the subject invention can also be manufactured by using multi stage injection molding (Woolfson et al. (1999), *J of Contr. Release* 61. 319-328; Malcolm et al. (2003), *J. Contr. Release* 91: 355-364, Woolfson et al. (2003), *J. Contr. Release* 91: 465-476).

The thermoplastic polymer that can be used in practicing the invention may in principle be any thermoplastic polymer or elastomer material suitable for pharmaceutical use, such as low density polyethylene, ethylene-vinyl acetate copolymers, poly(ether urethane), styrene-butadiene-styrene copolymers and polysiloxanes. In a specific embodiment, ethylene-vinyl acetate copolymer (poly-EVA) is used due to its excellent mechanical and physical properties. The poly-EVA material may be used for the core, the intermediate layer as well as the skin and can be any commercially available ethylene-vinyl acetate copolymer, such as the products available under the trade names: Elvax, Evatane, Lupolen, Movriton, Ultrathene, Ateva and Vestypar.

In one embodiment both core and intermediate layer are made out of the same polymer grade. In another embodiment, the core and the intermediate layer are not made out of the same polymer grade. Electing different polymer grades for core and intermediate layer, provides a means to adjust the release rates of drug compounds from the drug delivery system and allows fine-tuning of the flexibility of the system of the invention.

The vaginal ring according to the invention can be manufactured in any size as required. The same applies to the other shapes.

In one embodiment, the ring has an outer diameter (outer circumference) of between 50 and 60 mm and in another embodiment between 52 and 56 mm; the cross sectional diameter is between about 2.5 and 6.0 mm, in one specific embodiment between about 3.0 and 4.5 mm, in another embodiment between about 3.5 and 4.0 mm, in yet another embodiment the cross sectional diameter of the vaginal ring is 4.0 mm.

An implant suitably has a length of 1 to 6 cm and a diameter of 1-4 mm, preferably a length of 1-5 cm and a diameter of 1-3 mm, more preferably a length of 2-5 cm and a cross sectional diameter of 1.5 to 2.5 mm.

Intra-uterine systems (IUS) are medicated intra-uterine devices. They can take various shapes. In one embodiment the hormone loaded part consist of a fiber according to the invention. In a further embodiment the system is t-shaped. The hormone can then be loaded in the stem and/or arms of the system. Furthermore, such intrauterine systems can comprise a carrier which contains a hormone loaded fiber.

The drug reservoir dimensions of an IUS usually vary between 1 to 3.6 cm in length with a diameter of 1 to 4.5 mm, preferably a length of 1 to 3.6 cm and a diameter of 1.5 to 3.6 mm, more preferably a length of 2 to 3.6 cm and a diameter of 1.5 to 2.5 mm, even more preferably a length of 2.5 to 3.1 mm and a diameter of 2.0 to 2.3 mm. Either or both parts of the T may be medicated.

Another object of the present invention is to increase the efficiency of the drug substances employed in the drug delivery system, such as a vaginal ring, and to minimize the remnant drug content in the used system. The remnant content of both drug A and drug B in a ring system of the invention after use can be minimized to about 45 wt % or less of the amount loaded. Specifically, it can be reduced to about 20-35% by weight.

It is also an object of the subject invention to provide an improved vaginal ring in which the intermediate layer and/or the core, in addition to steroids for e.g. contraception or hormone replacement also comprises anti-microbials, e.g. to concomitantly treat and/or prevent sexually-transmitted diseases (STDs) such as HIV, herpes, chlamydia and gonorrhea.

In the ring embodiment of the subject invention, the surface of the body (external surface of the ring) is more than 800 $mm^2$, and in another embodiment more than 1000 $mm^2$ and will typically be in the order of 1700-2200 mm², though significantly larger surfaces are possible with some of the substantially ring-shaped forms, e.g. helically coiled spirals, provided that the design (physical dimensions) of the vaginal ring does not cause inconvenience for the subject human or animal.

It may sometimes be required to add a second compartment, which is a placebo compartment or a compartment loaded with one or more other drugs. Such an extra compartment can be necessary to administer, in addition to the steroids, anti-microbial drugs to treat and/or prevent STDs such as AIDS, chlamydia, herpes and gonorrhea.

Any anti-microbial drug can be incorporated into a drug delivery system, in particular a vaginal ring, of the subject invention (in the intermediate layer and/or in the core and/or in an additional compartment). The anti-microbial drug can be any anti-bacterial drug such as any antibiotic, any anti-viral agent, any anti-fungal agent or any anti-protozoal agent. An example of an anti-microbial drug contemplated to be incorporated into the vaginal ring of the subject invention is mandelic acid condensation polymer (Zanefeld et al. (2002), *Fertility and Sterility* 78(5): 1107-1115). Another example is dapivirine (4-[[4-[2,4,6-trimethylphenyl)amino-2-pyrimidinyl]amino]benzonitrile).

The vaginal ring and all other drug delivery systems according to the invention are physically stable.

As used herein, a physically stable drug delivery system (such as a ring) is a system, which can be stored at about 18° C.-40° C. for at least about half a year to one year without steroid crystal formation on the surface of the skin of the vaginal ring The vaginal ring according to the invention is primarily designed for contraceptive use, however the ring may also be used under certain conditions in HRT (hormonal replacement therapy), regulation of ovarian function, and so forth. Implants are also suitable for contraceptive use and may be even more convenient since they can remain in the body for several years without the necessity of daily, weekly or monthly compliance with the intake schedule.

The drug delivery system of the invention, in particular the vaginal ring, may also be used to concomitantly provide contraception and combat microbial disease. The microbial infection to be treated and/or prevented can be any bacterial, viral, fungal or protozoal infection. Specifically, sexually transmitted diseases such as HIV, chlamydia, gonorrhea, or herpes may be treated by incorporation of an anti-microbial agent into the system of the subject invention.

It is a further object of the invention to provide a method of contraception, which comprises the steps of positioning a drug delivery system of the subject invention within the female vaginal tract and retaining the system within the vaginal tract for a prolonged period of time. An implant is not positioned in the vaginal tract but is introduced subcutaneously, for example in the arm. A method of contraception with an implant thus comprises the steps of positioning a drug delivery system of the subject invention subcutaneously in the female and retaining the system within the female for a prolonged period of time.

As used herein "a prolonged period of time" for a ring-shaped system can be any time from about 7 to about 365 days. In one embodiment, the period of time is about 21 days. In another embodiment, the period is about 24 days. In a still further embodiment, the period can correspond with a calendar month and be either 22, 23, 24, 25, 26, 27, 28, 29, 30 or 31 days depending on the specific calendar month as well as the desired ring-free period (which will generally range from 0 to at maximum 7 days).

In other embodiments, the period of time is about 7, 14, 22, 23, 25, 26, 27, 28, 29, 30, 31, 42, 48, 59, 60, 61, 62, 63, 72, 84, 90, 91, 92, 96, 105, 120, 126, 144, 147, 151, 152, 153, 168, 181, 182, 184, 189, 192, 210, 212, 213, 214, 216, 231, 240, 252, 264, 273, 274, 288, 294, 304, 305, 312, 315, 334, 335, 336, 357, 360, 365 or 366 days.

For an implant, "a prolonged period of time" can be much longer and vary between 7 days and 5 years, in particular 7 days to 1 year or 7 days to 2 years or 7 days to 3 years or 7 days to 4 years or 7 days to 5 years.

For an IUS, "a prolonged period of time" can vary between 7 days and 5 years, in particular 7 days to 1 year or 7 days to 2 years or 7 days to 3 years or 7 days to 4 years or 7 days to 5 years.

For use in the vaginal tract the drug delivery device of the invention is in particular ring-shaped, such as rings, helical coils and springs, or T-shaped, in particular IUSs. Implants are used subcutaneously, in particular in the arm.

The invention further provides a method of contraception, which comprises the steps of positioning a drug delivery system of the subject invention within the female vaginal tract and retaining the system within the vaginal tract for at least approximately 21 days.

The invention further provides a method of contraception, which comprises the steps of positioning a drug delivery system of the subject invention within the female vaginal tract and retaining the system within the vaginal tract for at least approximately 24 days.

The invention further provides a method of contraception, which comprises the steps of positioning a drug delivery system of the subject invention within the female vaginal tract and retaining the system within the vaginal tract for at least approximately 28 days.

The invention further provides a method of contraception, which comprises the steps of positioning a drug delivery system of the subject invention within the female vaginal tract and retaining the system within the vaginal tract for at least approximately one calendar month-(varied from 28 to 31 days depending on the calendar month).

It is another object of the subject invention to provide a method of concomitantly providing contraception and treating or preventing a sexually transmitted disease which comprises the steps of positioning a drug delivery system of the subject invention within the female vaginal tract and retaining the system within the vaginal tract for at least approximately 21 days.

It is another object of the subject invention to provide a method of concomitantly providing contraception and treating or preventing a sexually transmitted disease which comprises the steps of positioning a drug delivery system of the subject invention Within the female vaginal tract and retaining the system within the vaginal tract for at least approximately 24 days.

The invention further provides a method of concomitantly providing contraception and treating or preventing a sexually transmitted disease, which comprises the steps of positioning a drug delivery system of the subject invention within the female vaginal tract and retaining the system within the vaginal tract for at least approximately 28 days.

The invention further provides a method of concomitantly providing contraception and treating or preventing a sexually transmitted disease, which comprises the steps of positioning a drug delivery system of the subject invention within the female vaginal tract and retaining the system within the vaginal tract for at least approximately one calendar month (varied from 28 to 31 days depending on the calendar month).

In one embodiment, the drug delivery system, in particular the vaginal ring or any other substantially ring-shaped form that is placed in the vaginal tract, is removed after about 21 days for an approximate one week period to permit menstruation. In another embodiment, the drug delivery system is removed after about 24 days for an approximate 4 day period to permit menstruation.

In other embodiments, the drug delivery system is removed after about 22, 23, 25, 26, 27, 28, 29, 30, 31, 42, 48, 59, 60, 61, 62, 63, 72, 84, 90, 91, 92, 96, 105, 120, 126, 144, 147, 151, 152, 153, 168, 181, 182, 184, 189, 192, 210, 212, 213, 214, 216, 231, 240, 252, 264, 273, 274, 288, 294, 304, 305, 312, 315, 334, 335, 336, 357, 360, 365 or 366 days. for a period to permit menstruation. After the period to allow for menstruation, a new drug delivery system of the subject invention is inserted into the female vagina to provide contraception in the next female cycle or cycles.

In other embodiments the drug delivery system is replaced immediately without allowing for a period to permit menstruation.

In a specific embodiment, a drug delivery system of the subject invention can be used in a calendar regimen as described in WO2007/001888, which is incorporated herein by reference.

In another embodiment, a drug delivery system of the subject invention can be used in an extended regimen, i.e. after removal of a ring after e.g. 21 or e.g. 24 days, the next ring is inserted the next day without allowing for a period to menstruate. Such extended regimens are well known in the art (see e.g. Davies et al., Contraception 46, 269-278 (1992)).

The subject invention further envisions a use of a drug delivery system of the subject invention for the manufacture of a contraceptive kit.

The subject invention further encompasses a use of a drug delivery system of the subject invention for the manufacture of a treatment for hormone replacement therapy.

The subject invention also provides a use of a drug delivery system of the subject invention for the manufacture of a combination preparation to provide contraception and to treat and/or prevent a sexually transmitted disease such as for example AIDS, herpes, chlamydia and gonorrhea.

In one embodiment of the subject invention both pharmaceutically active compounds are steroids. In a specific embodiment of the invention, one of the steroidal compounds is a progestogenic steroidal compound and the other steroidal compound is an estrogenic steroidal compound.

The progestogenic steroidal compound of the subject invention can be any suitable progestogen, having a relatively poor solubility in thermoplastic polymers such as EVA polymers and requiring a relatively high load in the polymeric matrix in order to achieve the desired release ratio. Examples of such progestogenic steroidal compounds include, but are not limited to, nomegestrol acetate (NOMAc), natural progesterone, Dydrogesterone, Medrogestone, Medroxyprogesterone acetate, megestrol acetate, chlormadinone acetate, cyproterone acetate, Gestonorone caproate, Demegestone, promegestone, nestorone, trimegestone, Norethisterone (=norethindrone), norethisterone acetate, lynestrenol, ethinodiol acetate, norethinodrel, Norgestrel, norgestimate, Dienogest, Etonogestrel, Levonorgestrel, Drospirenone, or any other suitable steroidal compound with progestogenic activity.

The estrogenic steroidal compound of the subject invention can be any suitable estrogen, having a relatively poor solubility in EVA polymers and requiring a relatively high load in the polymeric matrix in order to achieve the desired release ratio. Examples of such estrogenic steroidal compounds include, but are not limited to, Estradiol (E2), Ethinyl Estradiol (EE), Estriol, Estetrol (E4) or esters thereof, pseudopolymorphs thereof, pharmaceutically acceptable solvates thereof; hydrates thereof or hemihydrates thereof such as, but not limited to, estradiol hemihydrate, or any other suitable steroidal compound with estrogenic activity.

In a specific embodiment of the subject invention, the progestogen is nomegestrol acetate (NOMAc) and the estrogen is estradiol (E2) or a hydrate thereof such as estradiol hemihydrate.

In one embodiment of the subject invention, the progestogen is present in the intermediate layer at about 10-70% by weight and estrogen is present in the core as about 3-70% by weight. In one specific embodiment of the subject invention, nomegestrol acetate (NOMAc) is present in the intermediate layer at about 20-60% by weight. In another specific embodiment nomegestrol acetate (NOMAc) is present in the intermediate layer at about 35-60% by weight. In yet another embodiment, estradiol (E2) is present in the core as about 3-20% by weight. In still another specific embodiment estradiol (E2) is present in the core as about 4.5-9% by weight.

In another embodiment of the subject invention, the estrogen is present in the intermediate layer at about 3-70% by weight and the progestogen is present in the core as about 5-70% by weight. In one specific embodiment of the subject invention, estradiol (E2) is present in the intermediate layer at about 3-27% by weight. In another specific embodiment estradiol (E2) is present in the intermediate layer at about 9-27% by weight. In yet another embodiment estradiol (E2) is present in the intermediate layer at about 4-15% by weight. In still another embodiment nomegestrol acetate (NOMAc) is present in the core as about 5-35% by weight. In one specific embodiment nomegestrol acetate (NOMAc) is present in the core at about 35% by weight. In yet another embodiment nomegestrol acetate (NOMAc) is present in the core as about 5-15% by weight.

The three-layer vaginal ring of the invention may be designed to afford different ratios between the average release rates of the progestogenic steroidal compound and the estrogenic steroidal compound. The ratios between the average release rates may be significantly influenced by varying the location of the steroidal compounds, i.e. by loading the progestogen in the core and the estrogen in the intermediate layer or vice versa. In one specific embodiment, the progestogen is nomegestrol acetate (NOMAc), the estrogen is estradiol (E2) and the average release ratio between nomegestrol acetate (NOMAc) and estradiol (E2) may be varied as much as between about 0.6 and about 28.

In addition to steroids, also non-steroidal compounds may be included in the drug delivery system of the invention, in particular for administering two or more active compounds in a particular ratio.

The subject invention also provides a method of manufacturing the three-layered fiber that is used to make the drug delivery system of the subject invention by:

(i) producing a loaded (medicated) homogenous polymer core granulate
(ii) producing a loaded (medicated) homogenous polymer intermediate layer granulate; and
(iii) co-extruding the core granulate and the intermediate layer granulate with a polymer skin granulate to form the three-layered fiber.

The production of the loaded (medicated) homogenous polymer core granulate comprises:
a) grounding the core polymer;
b) dry powder mixing the grounded polymer with the active compounds to be loaded in the core;
c) blend extruding the resulting powder mixture of step (b);
d) cutting the resulting loaded polymer strands into granules, thereby obtaining a core granulate;
e) lubricating the core granulate with a lubricant.

The production of the loaded (medicated) homogenous polymer intermediate layer granulate comprises:
a) grounding the intermediate layer polymer;
b) dry powder mixing the grounded polymer with the active compounds to be loaded in the intermediate layer;
c) blend extruding the resulting powder mixture of step (b);
d) cutting the resulting loaded polymer strands into granules, thereby obtaining a intermediate layer granulate;
e) lubricating the intermediate layer granulate with a lubricant.

The present invention is further described in the following examples, which are not in any way intended to limit the scope of the invention as claimed.

EXAMPLES

Example 1

Preparation of the Three-Layered Ring

A wide variety of three-layered fibers were prepared (A1-A4, B1-B11 and C1-C7). The fibers were stretched to 4.0 mm from a single 3.6 mm capillary.

In order to mix the active ingredients nomegestrol acetate (NOMAc) and estradiol hemihydrate homogeneously through the polymer, two subsequent mixing steps were performed. In the first step, dry powder mixing was performed with the active compounds and polymer (EVA 28 or 33) powder. The active compounds were mixed with polymer powder in a stainless steel drum using a Rhonrad (Barrel-hoop principle) with a fixed rotation speed of approximately 47 rpm for 60 minutes. The first powder mixing step was performed by mixing the polymer and the active compound for the different active layers. Subsequently the homogenized powder mixtures were blend extruded using a 25 mm co-rotating double screw blend extruder (Berstorff ZE25) and the resulting medicated polymer strands were cut into granules using an IPS granulator. According to this process eight (8) active granulate batches were manufactured.

After granulation, all batches except granulate V, were lubricated with 0.1 wt % magnesium stearate in order to facilitate trico-extrusion. Batch V was manufactured by mixing 50 wt % of granulate U with 50 wt % placebo EVA 28. The compositions of the granulate batches that were used to manufacture the tri-layer fiber, using a co-extrusion process, are described in Table 1A and 1B below.

TABLE 1A

Active granulate compositions made of EVA 28 polymer

| | Material | | | |
|---|---|---|---|---|
| | Active granulate S | Active granulate T | Active granulate U | Active granulate V |
| Purpose | Either core or intermediate granulate | Intermediate granulate | Either core or intermediate granulate | Core granulate |
| Nomegestrol acetate | 35 wt % | 60 wt % | — | — |
| Estradiol | — | — | 9 wt % | 4.5 wt % |
| EVA 28 | 64.9 wt % | 39.9 wt % | 90.9 wt % | 95.45 wt % |
| Magnesium stearate | 0.1 wt % | 0.1 wt % | 0.1 wt % | 0.05 wt % |
| Total | 100.0 wt % | 100.0 wt % | 100.0 wt % | 100.0 wt % |

TABLE 1B

Active granulate compositions made of EVA 33 polymer

| | Material | | | |
|---|---|---|---|---|
| | Active granulate W | Active granulate X | Active granulate Y | Active granulate Z |
| Purpose | Intermediate granulate | Either core or intermediate granulate | Either core or intermediate granulate | Intermediate granulate |
| Nomegestrol acetate | 35 wt % | 35 wt % | — | — |
| Estradiol | 9 wt % | — | 9 wt % | 27 wt % |
| EVA 33 | 55.9 wt % | 64.9 wt % | 90.9 wt % | 72.9 wt % |
| Magnesium stearate | 0.1 wt % | 0.1 wt % | 0.1 wt % | 0.1 wt % |
| Total | 100.0 wt % | 100.0 wt % | 100.0 wt % | 100.0 wt % |

Tri-Layer Co-Extrusion

A Fourne Trico extruder (18/18/15 mm screws) was used for co-extrusion of the three-layered fiber. The two 18 mm extruders processed the core and intermediate material, while the 15 mm extruder was used to process the skin layer. The three extruders were connected with a 3-compartment spinning block with 3 separate spinning pumps. These pumps were used to control the volume flow rate of the three polymer melts. By controlling volume flow rate the layer thickness of all three layers was adjusted. The three polymer melt flows were combined in the spinneret to form a 3-layered fiber. A capillary of 3.6 mm was used. The target fiber diameter was 4.0 mm and all fibers were extruded at 110° C. at a speed of 1 m/min.

Fiber dimensions (outer diameter, intermediate thickness and skin thickness) were measured on 6 fiber pieces. The outer diameter was determined by means of laser thickness equipment. The layer thicknesses were determined using a microscope (Jena).

The following fiber batches were manufactured:

TABLE 2

Fiber dimensions

| Variant | Skin thickness [μm] | Skin material (placebo) | Intermediate layer thickness [μm] | Intermediate material | Core material | Fiber diameter [mm] |
|---|---|---|---|---|---|---|
| A1 | 50 | EVA 28 | 100 | W | EVA 28 (Placebo) | 4.00 |
| A2 | 150 | EVA 28 | 100 | W | EVA 28 (Placebo) | 4.00 |
| A3 | 50 | EVA 15 | 100 | W | EVA 28 (Placebo) | 4.00 |
| A4 | 50 | EVA 9 | 100 | W | EVA 28 (Placebo) | 4.00 |
| B1 | 50 | EVA 28 | 100 | X | Y | 4.00 |
| B2 | 150 | EVA 28 | 100 | X | Y | 4.00 |
| B3 | 100 | EVA 28 | 75 | S | U | 4.00 |
| B4 | 100 | EVA 28 | 100 | S | U | 4.00 |
| B5 | 100 | EVA 28 | 400 | S | U | 4.00 |
| B6 | 100 | EVA 28 | 800 | S | U | 4.00 |
| B7 | 150 | EVA 28 | 75 | S | U | 4.00 |
| B8 | 150 | EVA 28 | 100 | S | U | 4.00 |
| B9 | 250 | EVA 28 | 75 | S | U | 4.00 |
| B10 | 100 | EVA 28 | 75 | S | V | 4.00 |
| B11 | 100 | EVA 28 | 100 | T | U | 4.00 |
| C1 | 50 | EVA 28 | 100 | Y | X | 4.00 |
| C2 | 150 | EVA 28 | 100 | Y | X | 4.00 |
| C3 | 50 | EVA 28 | 200 | Y | X | 4.00 |
| C4 | 150 | EVA 28 | 100 | Z | X | 4.00 |
| C5 | 100 | EVA 28 | 100 | U | S | 4.00 |
| C6 | 100 | EVA 28 | 400 | U | S | 4.00 |
| C7 | 100 | EVA 28 | 800 | U | S | 4.00 |

Figure 1B:
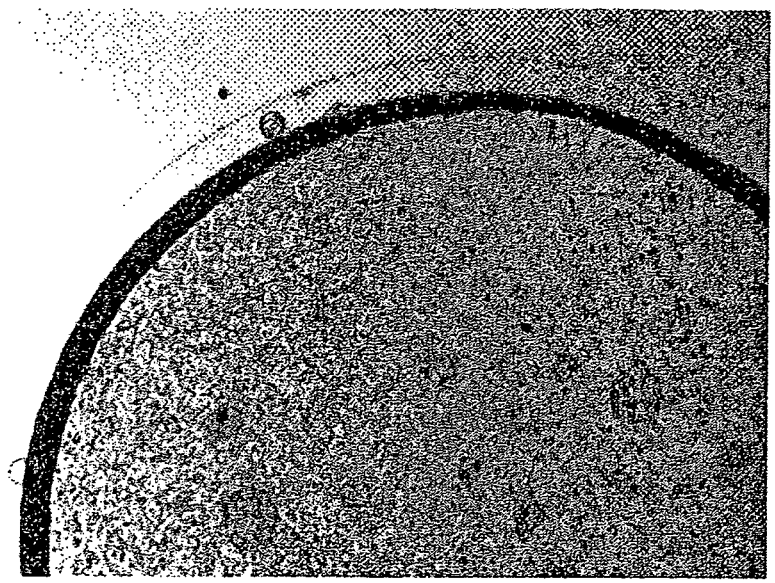
Figure 1C:
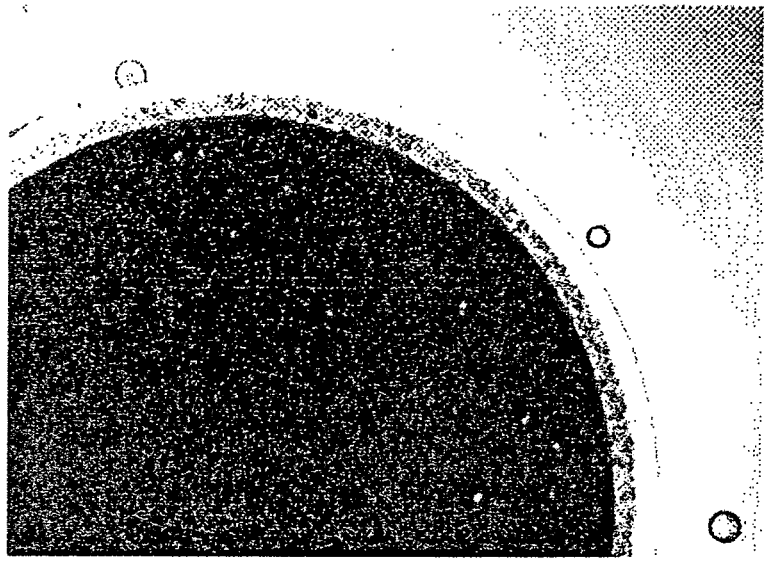

Photographs of typical examples of tri-axial cross-sections of variants A, B and C are provided in FIG. 1A, FIGS. 1B and 1C, respectively.

Cutting and Assembly

After co-extrusion, the three-layered fiber batches A1-A4, B1, B2, C1-C4 were cut into pieces of 157 mm. Rings were formed by gluing the fiber ends together using a Loctite polyolefin gluing kit (Loctite 406+Loctite 770).

The three-layered fiber batches B3-B11 and C5-7 were cut into pieces of 157 mm after which they were welded with flash free welding machines (CCM) at a welding temperature of 115° C. and a welding time of 17 seconds.

Example 2

In-Vitro NOMAc and Estradiol Release Rates

In-Vitro Release Rates

Figure 2:
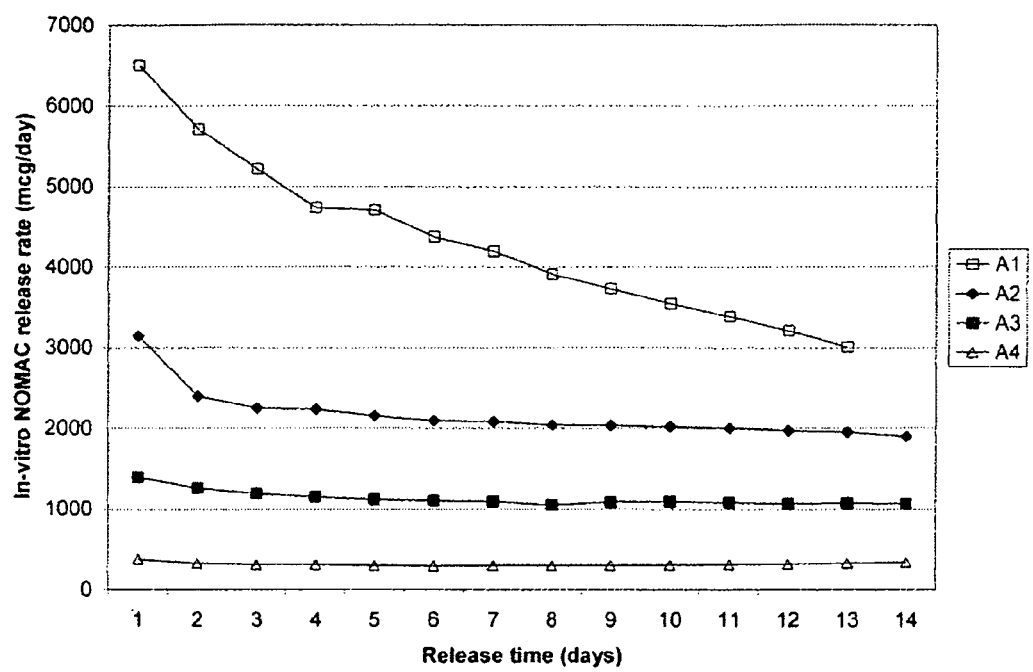
FIG. 2 shows the in-vitro nomegestrol acetate (hereinafter referred to as NOMAc) release profiles of ring designs of variant A1-A4.
Figure 3:
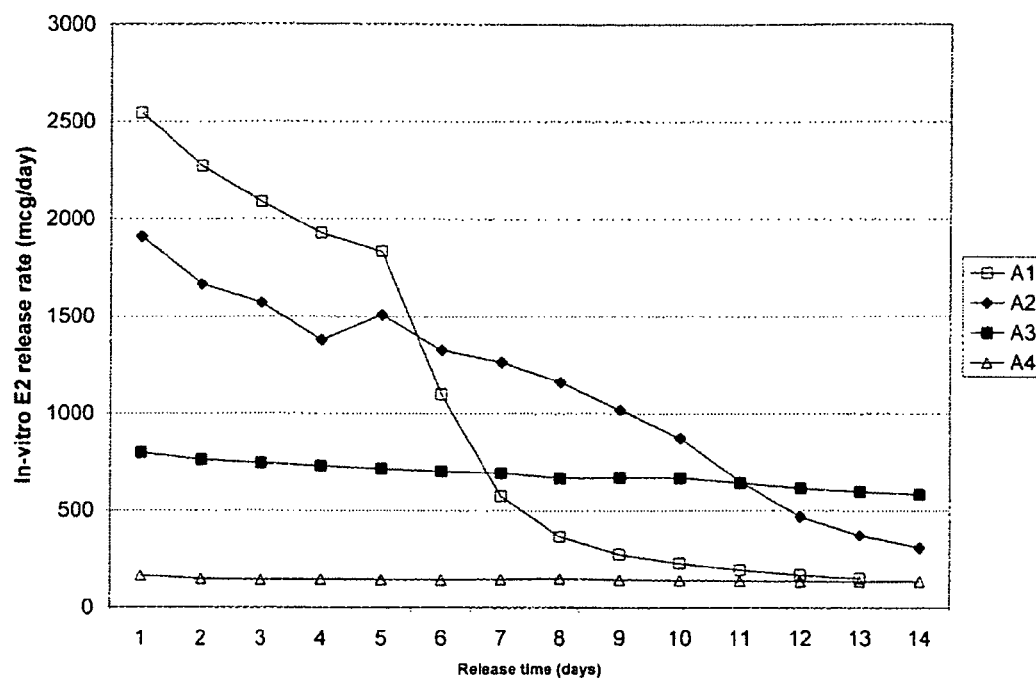
FIG. 3 shows the in-vitro Estradiol (E2) release profiles of ring designs of variant A1-A4.
Figure 4:
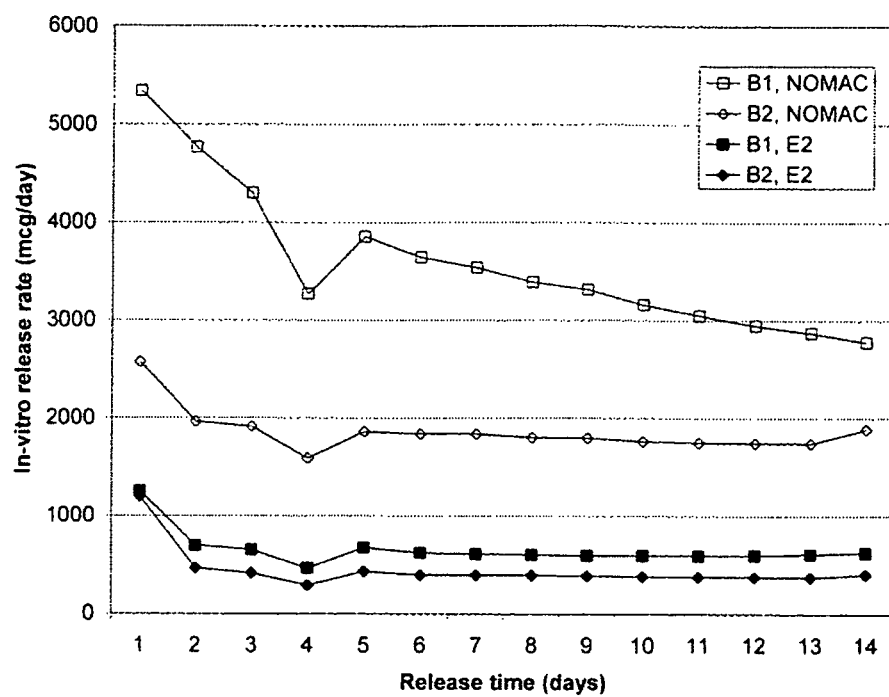
FIG. 4 shows the in-vitro NOMAc and Estradiol (E2) release profiles of ring designs of variant B1 and B2.
Figure 5A:
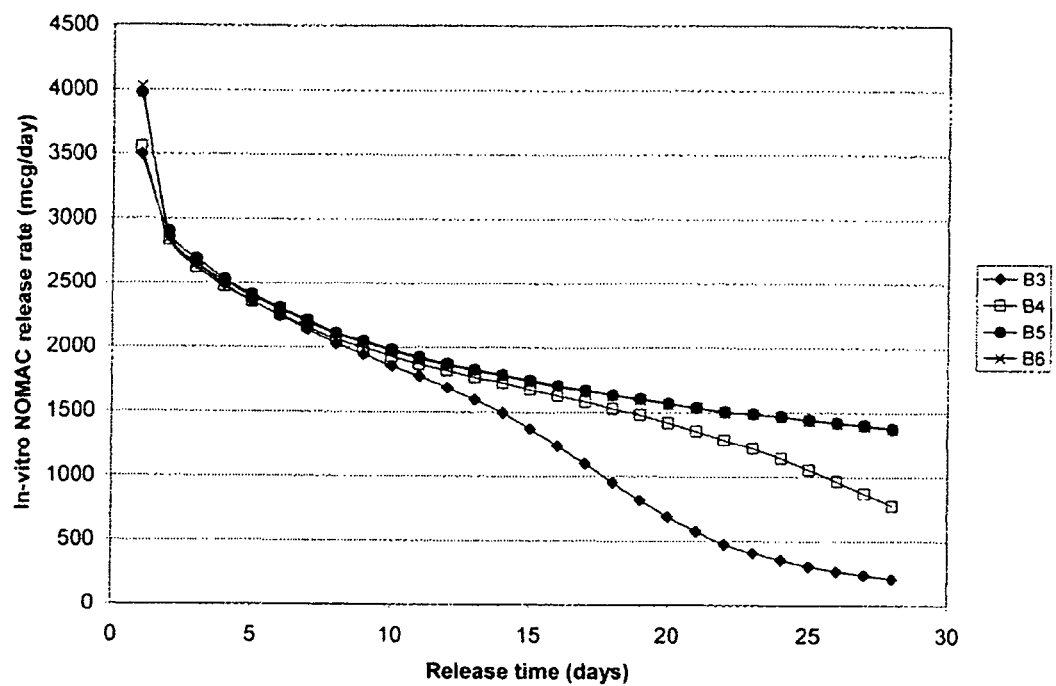
FIGS. 5A and 5B shows the in-vitro NOMAc release profiles of ring designs of variant B3-B11.
Figure 5B:
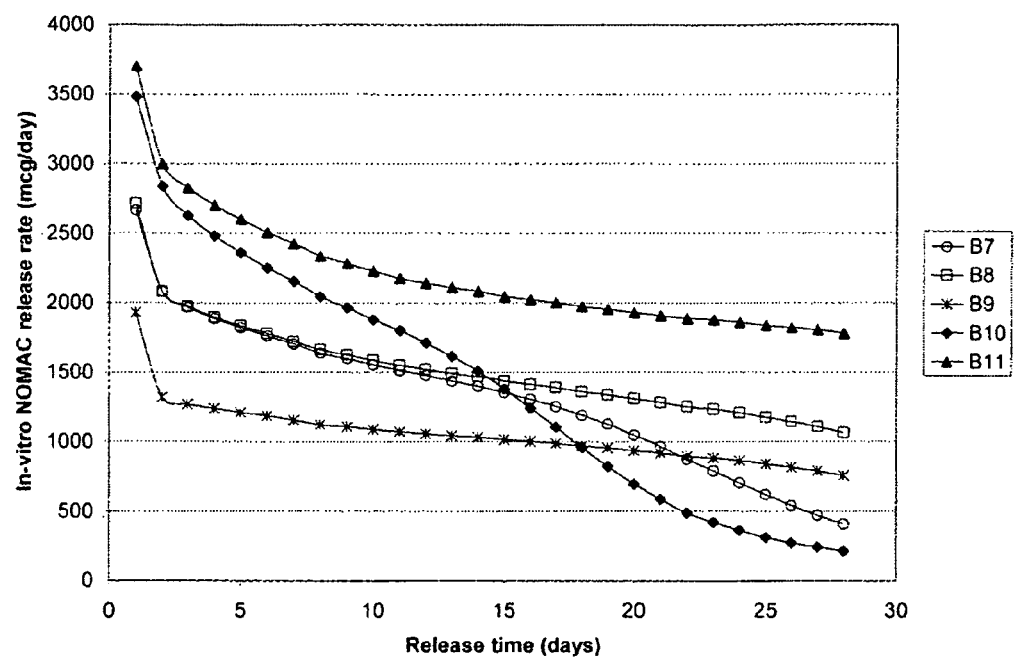
Figure 6A:
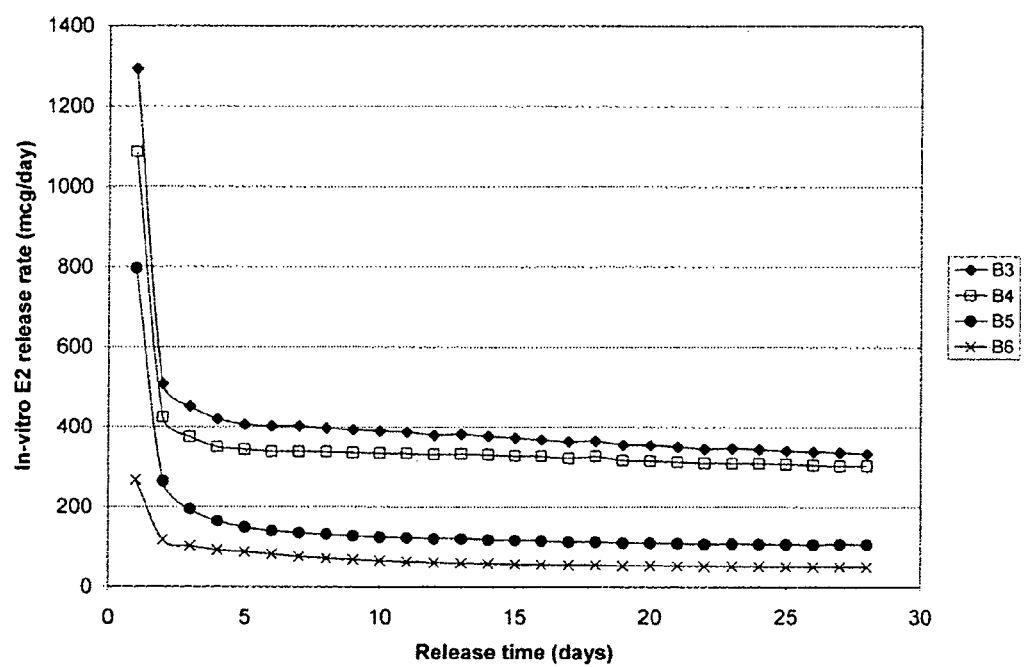
FIGS. 6A and 6B shows the in-vitro Estradiol (E2) release profiles of ring designs of variant B3-B11.
Figure 6B:
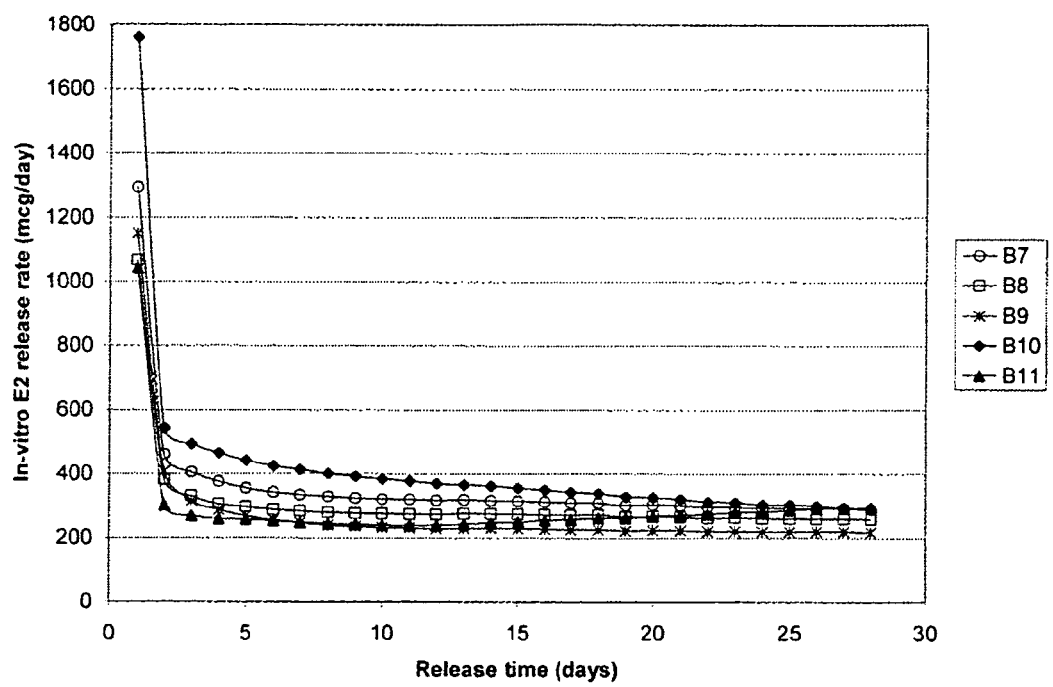
Figure 7:
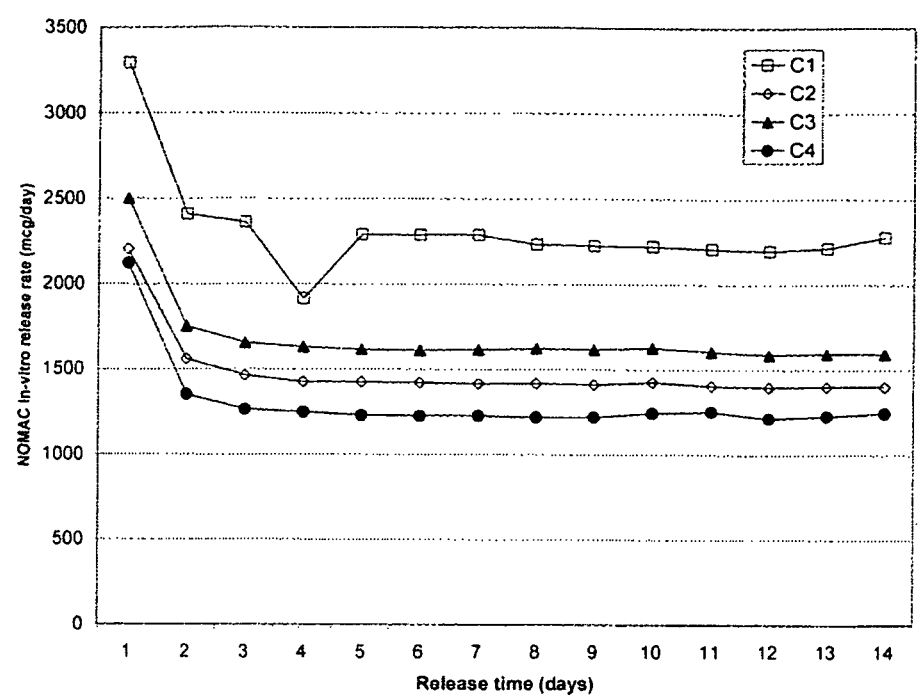
FIG. 7 shows the in-vitro NOMAc release profiles of ring designs of variant C1-C4.
Figure 8:
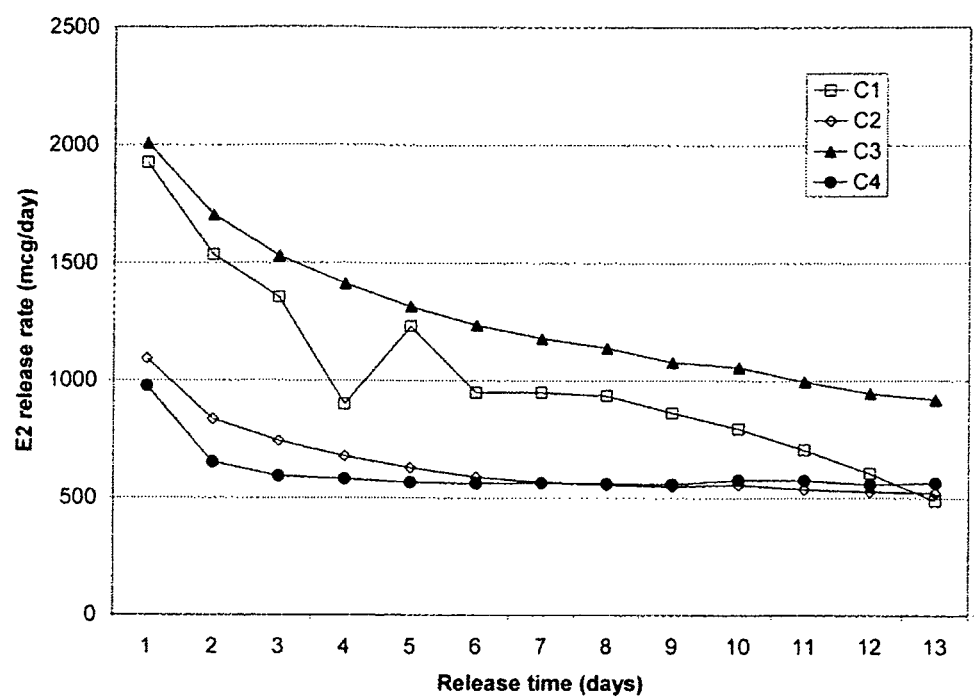
FIG. 8 shows the in-vitro Estradiol (E2) release profiles of ring designs of variant C1-C4.

Results for in-vitro release for rings partially made of EVA 33 are shown in Table 3A and FIGS. 2 to 4, 7 and 8. FIG. 2 shows the in-vitro NOMAc release profiles of ring designs of variant A. FIG. 3 shows the in-vitro Estradiol release profiles of ring designs of variants A. FIG. 4 shows the in-vitro NOMAc and Estradiol release profiles of ring designs of variants B1-B2. FIG. 7 shows the in-vitro NOMAc release profiles of ring designs of variants C1-C4. FIG. 8 shows the in-vitro Estradiol release profiles of ring designs of variants C1-C4. Table 3A shows the release rates from four (4) samples of ring variant A, two (2) samples of ring variant B and four (4) samples of ring variant C.

TABLE 3A

In-vitro NOMAc and Estradiol release rates in water/sodium lauryl sulphate (SLS) (0.9%) of systems with EVA 33

| | NOMAc release [μg/day] | | | Estradiol (E2) release [μg/day] | | |
|---|---|---|---|---|---|---|
| Batch: | Day 1 | Average day (2-13) | Day 13 | Day 1 | Average day (2-13) | Day 13 |
| A1 | 6504 | 4146 | 3009 | 2545 | 932 | 151 |
| A2 | 3151 | 2105 | 1955 | 1911 | 1106 | 374 |
| A3 | 1395 | 1115 | 1075 | 799 | 686 | 600 |
| A4 | 376 | 309 | 328 | 165 | 144 | 135 |
| B1 | 5337 | 3510 | 2873 | 1254 | 611 | 611 |
| B2 | 2573 | 1801 | 1744 | 1200 | 393 | 376 |
| C1 | 3294 | 2239 | 2214 | 1925 | 943 | 489 |

TABLE 3A-continued

In-vitro NOMAc and Estradiol release rates in water/sodium lauryl sulphate (SLS) (0.9%) of systems with EVA 33

| Batch: | NOMAc release [µg/day] | | | Estradiol (E2) release [µg/day] | | |
|---|---|---|---|---|---|---|
| | Day 1 | Average day (2-13) | Day 13 | Day 1 | Average day (2-13) | Day 13 |
| C2 | 2207 | 1432 | 1401 | 1094 | 608 | 523 |
| C3 | 2503 | 1629 | 1596 | 2008 | 1210 | 919 |
| C4 | 2124 | 1245 | 1228 | 977 | 577 | 565 |

Figure 9:
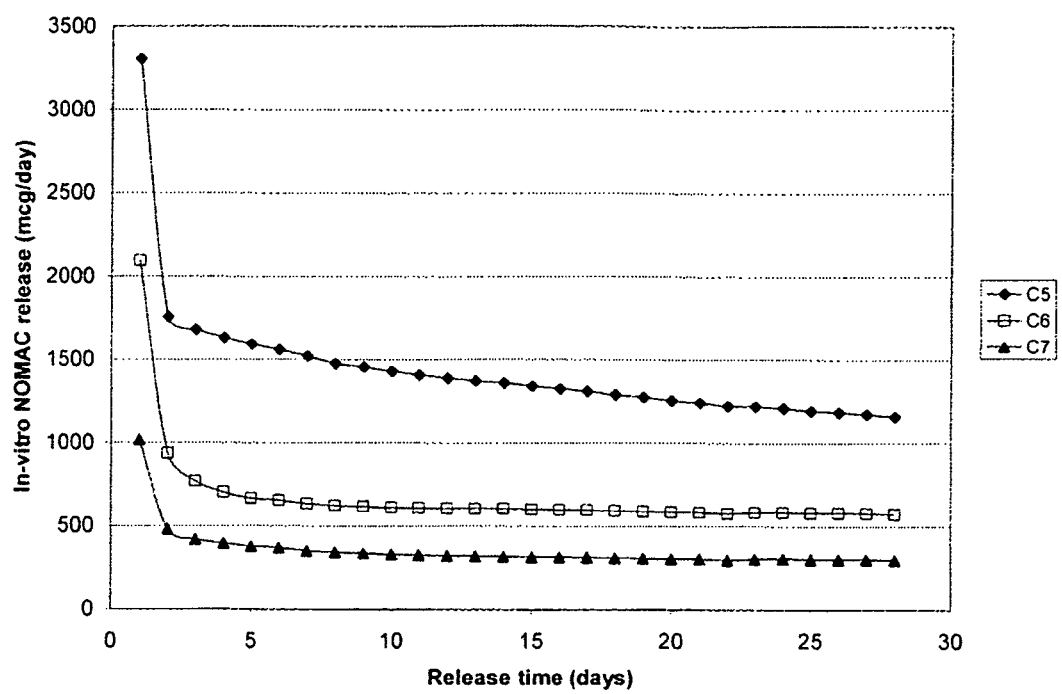
FIG. 9 shows the in-vitro NOMAc release profiles of ring designs of variant C5-C7.
Figure 10:
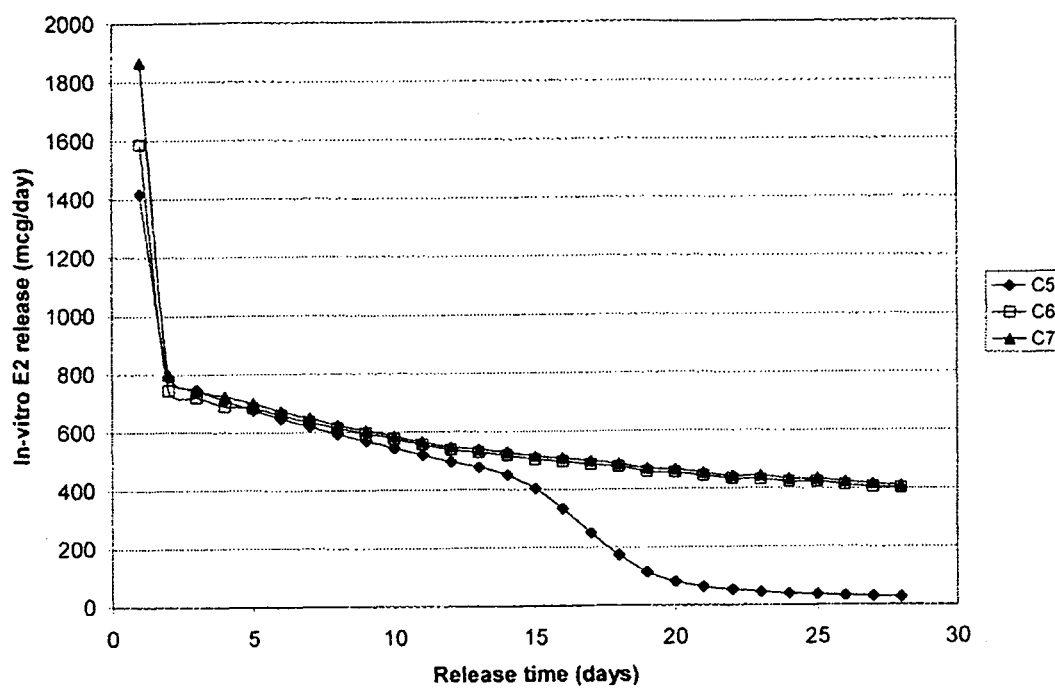
FIG. 10 shows the in-vitro Estradiol (E2) release profiles of ring designs of variant C5-C7.

Results for in-vitro release for rings fully composed of EVA 28 are shown in Table 3B and FIGS. 5, 6, 9 and 10. FIGS. 5A and 5B show the in-vitro NOMAc release profiles of ring designs of variants B3-B11. FIGS. 6A and 6B show the in-vitro Estradiol release profiles of ring designs of variants B3-B11. FIG. 9 shows the in-vitro NOMAc release profiles of ring designs of variant C5-C7. FIG. 10 shows the in-vitro Estradiol release profiles of ring designs of variant C5-C7. Table 3B shows the release rates from nine (9) samples of ring variant B fully composed of EVA 28 and three (3) samples of ring variants C fully composed of EVA 28.

TABLE 3B

In-vitro NOMAc and Estradiol release rates in water/sodium lauryl sulphate (SLS) (0.9%) of systems with EVA 28

| Batch: | NOMAc release [µg/day] | | | Estradiol (E2) release [µg/day] | | |
|---|---|---|---|---|---|---|
| | Day 1 | Average day (2-14) | Day 14 | Day 1 | Average day (2-14) | Day 14 |
| B3 | 3500 | 2088 | 1495 | 1294 | 408 | 378 |
| B4 | 3556 | 2145 | 1729 | 1087 | 347 | 331 |
| B5 | 3977 | 2203 | 1792 | 797 | 148 | 118 |
| B6 | 4026 | 2186 | 1785 | 268 | 78 | 59 |
| B7 | 2666 | 1680 | 1400 | 1294 | 348 | 317 |
| B8 | 2714 | 1708 | 1469 | 1067 | 294 | 275 |
| B9 | 1929 | 1146 | 1032 | 1152 | 263 | 231 |
| B10 | 3482 | 2097 | 1509 | 1761 | 418 | 363 |
| B11 | 3703 | 2419 | 2083 | 1043 | 253 | 248 |
| C5 | 3308 | 1512 | 1362 | 1419 | 603 | 451 |
| C6 | 2096 | 667 | 606 | 1588 | 620 | 518 |
| C7 | 1021 | 361 | 319 | 1868 | 637 | 528 |

Release Ratio between NOMAc and Estradiol

The ratios between the two drug substances for variants A, B and C are provided in Tables 4A and 4B. For the rings in Table 4A the ratio between the two drug substances was determined by dividing the average in-vitro release rates (day 2-5) of NOMAc by the average release rate of Estradiol. For the rings in Table 4B (fully made of EVA 28) the ratio was determined by dividing the average release rates from 2-14 days.

TABLE 4A

Release Ratio between in-vitro NOMAc and Estradiol release rates in ring composed of EVA 33

| Batch | Average NOMAc day 2-5 release [µg/day] | Average Estradiol day 2-5 release [µg/day] | Ration between NOMAc and Estradiol |
|---|---|---|---|
| A1 | 5095 | 2030 | 2.5 |
| A2 | 2260 | 1531 | 1.5 |
| A3 | 1181 | 739 | 1.6 |
| A4 | 313 | 146 | 2.1 |

TABLE 4A-continued

Release Ratio between in-vitro NOMAc and Estradiol release rates in ring composed of EVA 33

| Batch | Average NOMAc day 2-5 release [µg/day] | Average Estradiol day 2-5 release [µg/day] | Ration between NOMAc and Estradiol |
|---|---|---|---|
| B1 | 4050 | 625 | 6.5 |
| B2 | 1833 | 404 | 4.5 |
| C1 | 2245 | 1256 | 1.8 |
| C2 | 1469 | 722 | 2.0 |
| C3 | 1664 | 1490 | 1.1 |
| C4 | 1274 | 599 | 2.1 |

TABLE 4B

Release Ratio between in-vitro NOMAc and Estradiol release rates in ring fully composed of EVA 28

| Batch | Average NOMAc day 2-14 release [µg/day] | Average Estradiol day 2-14 release [µg/day] | Ration between NOMAc and Estradiol (day 2-14 release) |
|---|---|---|---|
| B3 | 2088 | 408 | 5.1 |
| B4 | 2145 | 347 | 6.2 |
| B5 | 2203 | 148 | 14.9 |
| B6 | 2186 | 78 | 28.1 |
| B7 | 1680 | 348 | 4.8 |
| B8 | 1708 | 294 | 5.8 |
| B9 | 1146 | 263 | 4.4 |
| B10 | 2097 | 418 | 5.0 |
| B11 | 2419 | 253 | 9.5 |
| C5 | 1512 | 603 | 2.5 |
| C6 | 667 | 620 | 1.1 |
| C7 | 361 | 637 | 0.6 |

The ring designs of group B and C represent formulations wherein NOMAc and Estradiol crystals are physically/spatially separated and are present in two distinct layers. In variants B1-B11 the intermediate layer is loaded with NOMAc, whereas the core is loaded with Estradiol. In variants C1-C7, the intermediate layer is loaded with Estradiol, whereas the core is loaded with NOMAc. In both groups, the active ingredients are present in their solid (crystalline) state. In variants of group B, the ratio in average release rate between NOMAc and Estradiol can be increased up to 28.1, whereas the ratio in group C remains below 2.5 and can be substantially reduced to 0.6 by increasing the intermediate layer thickness.

Stabilization Effect of the Drug Delivery Device of the Invention

After the ring has been put in a sink, steroids start to diffuse out of the ring and the concentration of the steroids dissolved in the polymeric matrix drops slightly. As a consequence thereof, the solid steroids start to dissolve. Thus, the decrease of the concentration gradient due to diffusive transport out of the ring is counterbalanced by the dissolution of the steroid present in a solid form. FIGS. 2-10 illustrate this stabilizing effect. The slope of the release curve for variant B2 for NOMAc and variants B1 and B2 for Estradiol (E2) in FIG. 4, for variants C1 to C4 in FIG. 7 and for variants C3 to C4 in FIG. 8 is substantially flat, i.e. indicates that the release is almost zero order, i.e. the release rate of the steroid can be maintained until the solid phase is dissolved.

In the examples in which EVA 28 was used for dissolving NOMAc and Estradiol, a similar trend was found. In the B variations, the Estradiol release profile in FIG. 6 was close to zero order in all examples (B3-B11). Batches B7, B8 and B9 in FIG. 5 revealed also essentially flat release profiles for NOMAc and the other batches, though slightly less constant, also showed reasonable constant release profiles. In the variants C (C5-C7), the NOMAc release profiles in FIG. 9 are very flat even for relatively high release rates.

Example 3

Drug Substance Efficiency of the Drug Delivery Device of the Invention

Figure 11:
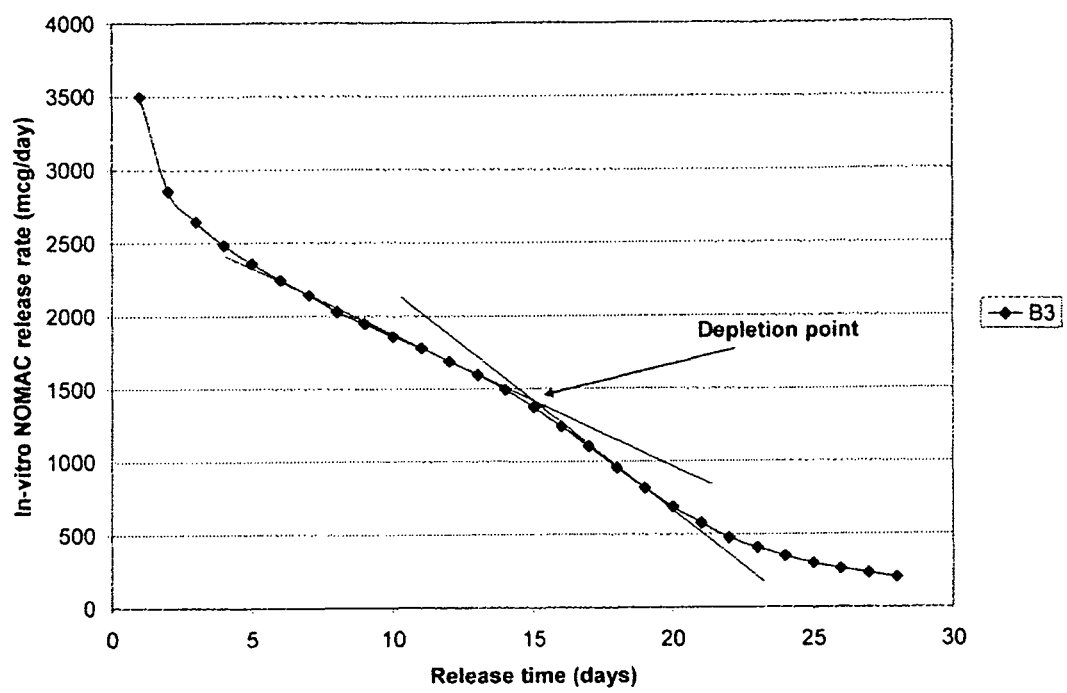
FIG. 11 shows the determination of the depletion point, used for the calculation of drug substance efficiency, from an in-vitro NOMAc release profile of ring design of variant B3.
Figure 12:
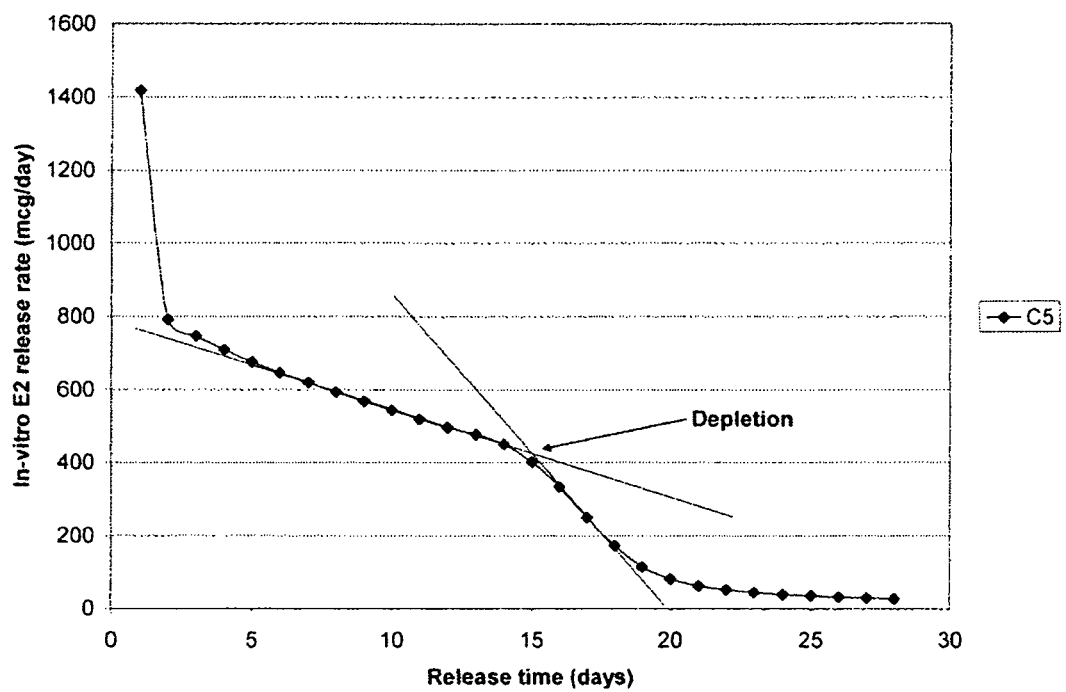
FIG. 12 shows the determination of the of the depletion point, used for the calculation of drug substance efficiency, from an in-vitro Estradiol (E2) release profile of ring design of variant C5.

In case the active compounds are largely present in their solid state, the drug substance efficiency of a ring can be largely improved. The release rate can be maintained until the solid phase is depleted. Determination of the point at which depletion of one of the steroids starts is shown in FIGS. 11 and 12. The release profile shows a (near) steady state regime until the curve deflects (S-curve) into another regime. The point where the two tangent lines of these regimes cross each other is defined as the point of depletion.

Table 5 shows drug substance efficiency for several of the batches (batches B3, B4, B7 and C5).

TABLE 5

Drug substance efficiencies of some example batches

| Batch | Depletion point (days) [drug substance] | Drug substance load [mg] | Drug substance efficiency |
|---|---|---|---|
| B3 | 14 [NOMAc] | 44 | 70 |
| B4 | 19 [NOMAc] | 58 | 68 |
| B7 | 18 [NOMAc] | 41 | 70 |
| C5 | 14 [Estradiol] | 12 | 78 |

From the data in Table 5 it can be derived that the release is essentially maintained until about 65-80% of the drug substance is released. The resulting remnant content after use is only 20-35% by weight.

Discussion of the Experimental Results

In-vitro release rates and Release Ratio between NOMAc and Estradiol

Variants A1 to A4 demonstrate that by loading both steroidal compounds in one layer the release ratio of NOMAc and Estradiol is confined within narrow margins in comparison to the wide range of release ratios, which can be achieved with a vaginal ring of the subject invention. Some variation in the release ratio is observed when comparing the examples A1, A2, A3 and A4; however varying the skin properties (thickness and/or polymer) does not provide a practical means to tune the release of two compounds independently from each other. The small variability in release ratio (between 1.5 and 2.5) observed for variants A1 to A4 is not linked with the overall absolute release rate of both steroidal compounds from the ring. (Table 4A). Consequently by varying the skin properties it is not possible to obtain, except by sheer coincidence, the desired optimal simultaneous release characteristics, which both include an optimal relative release ratio and an optimal absolute release rate.

Physical separation of the two crystalline steroids (by putting them in two distinct layers—variants B and C), provides the ability to tune the release rate of the two steroids independently. This is exemplified by variants B and C, which show that the release ratio between NOMAc and E2 can be adjusted over a considerable range in both directions. (up or down).

With regard to intermediate layer thickness, skin thickness and polymer grades the rings A1, B1 and C1 are identical, except for the location where the drug substance crystals are loaded (Table 2). The same counts for variants A2, B2 and C2.

The rings A1 and A2 are the reference rings in which the NOMAc and E2 crystals are both loaded in the intermediate layer and thus the drug crystals are not spatially separated. As for rings B1 and B2, in case these rings would behave in an ideal manner, the Estradiol release rate from rings B1 and B2 as compared with the reference rings should be quite substantially reduced due to fact that Estradiol is loaded in the core thus increasing the diffusion length for this compound. The NOMAc release on the other hand should remain unaffected (identical diffusion length). In practice the behavior of variants B1 and B2 appears to approach ideal behavior. When the Estradiol release of the rings B1 and B2 is compared with the release of the reference rings, the results (Table 4A) reveal that the average Estradiol release rate indeed has dropped quite significantly, by about 69% for B1 in comparison to A1 and by about 74% for B2 in comparison to A2. By comparison the NOMAc average release rate was much less affected, showing a moderate decline by about 15-20% for both B1 vs. A1 and B2 vs. A2. This has a large impact on the release ratio and the results in Table 4A demonstrate that the separation of the drug substance crystals of NOMAc and Estradiol in different layers significantly increases the ability to increase the release ratio. The NOMAC release rates of batches C1 and C2 are considerably lower as compared to A1 and A2, which is due to the longer diffusion length. The Estradiol release rates are lower as well (see Table 4A) in spite of a comparable diffusion length. This indicates that there is an interaction between the two steroids once the steroid from the core diffuses into the intermediate layer. Because the reduction in release rates was comparable for both steroids, the release ratio remains around 2.

Example C3 demonstrates the concept for tuning the release ratio in the other direction (low ratio's). Moreover this example demonstrates that varying of the intermediate layer thickness in combination with spatial separation of the drug crystals is a practical means to tune release rate and the release ratio between two compounds. Ring C3 is similar to ring C1 except that intermediate layer is twice as thick and hence the diffusion length for NOMAc is further increased. This further increase of the diffusion length for NOMAc results in a further decrease of the NOMAc release rate and thus in a value for the release ratio that is close to 1. This is further substantiated by the examples C5, C6 and C7. By largely increasing the intermediate layer thickness the ratio is reduced to even 0.6. In these examples, the E2 release rate remains unaffected while the NOMAC release rate is strongly reduced.

Similar effects were observed in the rings of variant B that were fully composed of EVA 28. By increasing the intermediate (NOMAC) layer thickness while maintaining the skin thickness, the ratio between NOMAC and Estradiol was increased from 5.1 to 28.1 (batches B3-B6), without interfering with the absolute NOMAC release rate. By only increasing the skin thickness (examples B3, B7 and B9) the ratio was maintained within a narrow bandwidth (4.4-5.1). However, the absolute release rates were indeed affected considerably by the change in skin layer thickness.

Overall, the type of EVA polymer chosen to disperse the active compounds (EVA 28 versus EVA 33) does not have a strong effect on the release ratio between the two steroids (compare B2 with B8).

Stabilization Effect of the Drug Delivery Device of the Invention

The absence of effect of drug load (after saturation concentration has been reached) is clearly substantiated by the examples. Varying the Estradiol load in either intermediate layer (C2 versus C4) or core (B3 versus B10) does not affect the absolute release rate considerably nor does it affect the relative ratio in which the compounds (NOMAc and Estradiol) are released. Also variations in the NOMAc concentration do not affect the absolute release rate substantially, though some effects on ratio can be observed.

The effect of increasing the drug load (above the point where the compound is present in the solid state) is illustrated by the batches C2 and C4. The Estradiol concentration in the intermediate layer of batches C2 and C4 is 9 wt % and 27 wt % respectively (in both examples Estradiol is present in the solid state). Although the Estradiol drug load is increased considerably (batch C2 versus C4) the increase does not affect the absolute release rate of Estradiol to a significant extent, nor does it affect the relative release rate (the release ratio between NOMAc and Estradiol). This example clearly demonstrates that the release rate is governed by the dissolved drug concentration, which in both cases will be essentially equal to the saturation concentration of Estradiol in the polymer and that a further increase of drug load is not a useful means to influence the release rate of a compound present in the solid state.

Comparison of the batches B3 and B10, in which the Estradiol load in the core is reduced from 9 wt % to 4.5 wt % (in both examples Estradiol is present in the solid state), confirm that the estradiol release cannot be adjusted by varying drug load above the level where Estradiol has crystallized out in the matrix. The inability to use drug load to tune release substantially is further underlined by comparing example B3 with B11. In this case the NOMAc drug load in the intermediate layer is increased from 35 wt % (B3) to 60 wt % (B11) and this increase has only a minor effect on the NOMAc release rate. The E2 release rate is reduced (B3 versus B11) and without being bound by theory this probably is the result of an increase diffusion resistance in the intermediate layer, which consists for about 60 wt % of drug substance crystals which are essentially impermeably for diffusing drug molecules and hence this also increases diffusion length due to the increased tortuosity of the diffusion path.

Drug Substance Efficiency of the Drug Delivery Device of the Invention

Figure 13:
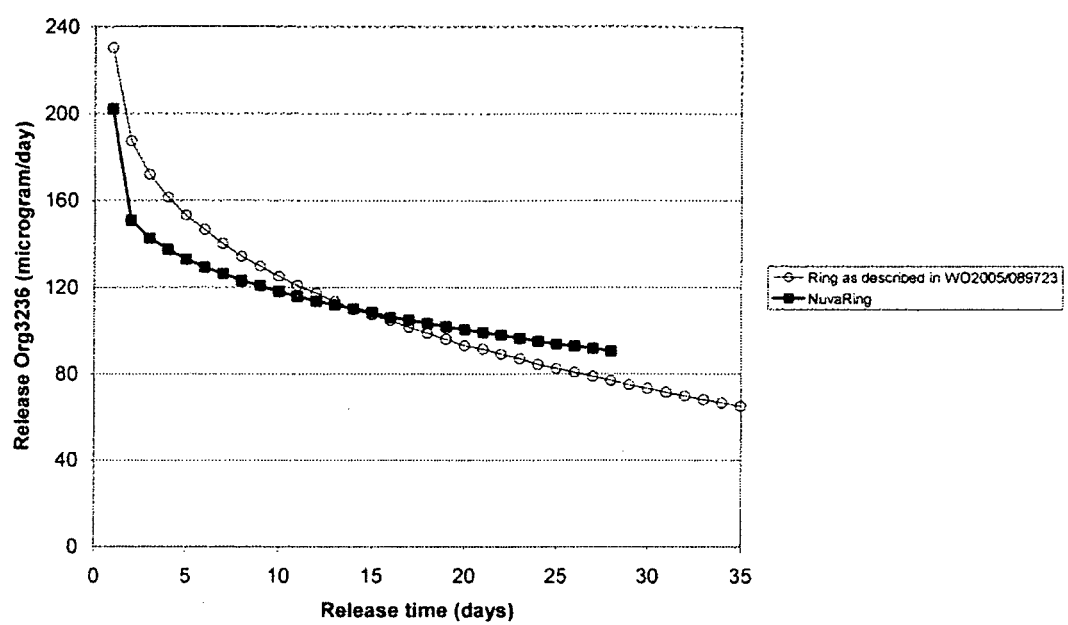
FIG. 13 shows the effect of changing the Etonogestrel concentration on the release profile of a two layered system containing only dissolved steroids (NuvaRing® and a ring as described in WO2005/089723).
Figure 14:
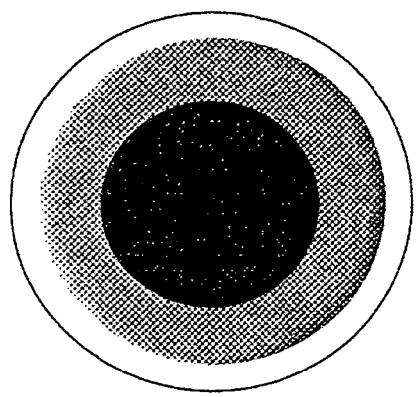
FIG. 14 shows a schematical cross section of the three-layer fiber.
Figure 15:
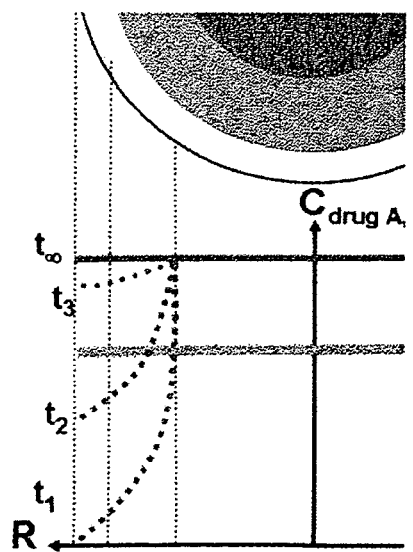
FIG. 15 shows in a graph the re-distribution and leveling of the internal concentration gradient of the fiber in FIG. 14.
Figure 16:
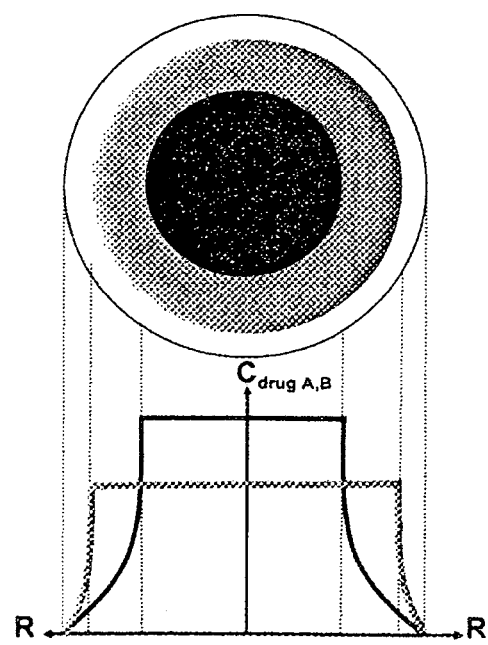
FIG. 16 is an illustration of the fully developed concentration gradient under steady state conditions.

The remnant content after use of the drug delivery device of the invention is only 20-35% by weight, which is considerably lower than the remnant content present in rings described in the prior art (U.S. Pat. No. 5,989,581; WO2004/103336). For rings in which the steroids are present in the dissolved form (EP 876 815, and WO2005/089723), a large reservoir (core and intermediate) needs to contain a certain concentration of steroid in order to reach a specific absolute release rate in combination with an acceptable flat profile. In case less steroid is dissolved, the absolute release rate can still be achieved by choosing the appropriate skin thickness and/or skin material. However, the observed release profile will be steeper (see FIG. 13). Putting more steroid in the ring in combination with maintaining the release rate (e.g. adjusting skin thickness) results in a less efficient ring. The three layer ring described in WO2004/103336, suitable for the simultaneous release of two or more compounds, contains at least one active compound which is completely dissolved in the polymer matrix. Similar to NuvaRing® this dissolved compound needs to be loaded in large excess in order to obtain reasonably constant profiles and hence like NuvaRing® this results in a sub-optimal drug substance efficiency for at least one of the active pharmaceuticals loaded in the ring.

Example 4

Preparation of the Three-Layered Ring

A wide variety of three-layered fibers were prepared (D1-D3, F1-F3, G1-G3). The fibers were stretched to 4.0 mm from a single 3.6 mm capillary.

In order to mix the active ingredients homogeneously through the polymer, two subsequent mixing steps were performed. In the first step, dry powder mixing was performed with the active compounds and polymer (EVA 28) powder. The active compounds were mixed with polymer powder in a stainless steel drum using a Rhonrad (Barrel-hoop principle) with a fixed rotation speed of approximately 47 rpm for 60 minutes. The first powder mixing step was performed by mixing the polymer and the active compound for the different active layers. Subsequently the homogenized powder mixtures were blend extruded using a 25 mm co-rotating double screw blend extruder (Berstorff ZE25) and the resulting medicated polymer strands were cut into granules using an IPS granulator. According to this process four active granulate batches were manufactured.

After granulation, all batches were lubricated with 0.1 wt % magnesium stearate in order to facilitate trico-extrusion. The compositions of the granulate batches that were used to manufacture the tri-layer fiber, using a co-extrusion process, are described in Table 6A below.

TABLE 6A

| Material | Active | Active content | EVA grade |
|---|---|---|---|
| Active granulate J | Drosperinone (DPN) | 20 wt % | EVA 28 |
| Active granulate K | Levonorgestrel (LNG) | 20 wt % | EVA 28 |
| Active granulate L | Etonogestrel (ETO) | 11 wt % | EVA 28 |
| Active granulate M | Estradiol (E2) | 10 wt % | EVA 28 |

Tri-Layer Co-Extrusion

A Fourne Trico extruder (18/18/15 mm screws) was used for co-extrusion of the three-layered fiber. The two 18 mm extruders processed the core and intermediate material, while the 15 mm extruder was used to process the skin layer. The three extruders were connected with a 3-compartment spinning block with 3 separate spinning pumps. These pumps were used to control the volume flow rate of the three polymer melts. By controlling volume flow rate the layer thickness of all three layers was adjusted. The three polymer melt flows were combined in the spinneret to form a 3-layered fiber. A capillary of 3.6 mm was used. The target fiber diameter was 4.0 mm and all fibers were extruded at a speed of 1-2 m/min.

Fiber dimensions (outer diameter, intermediate thickness and skin thickness) were measured on 6 fiber pieces. The outer diameter was determined by means of laser thickness equipment. The layer thicknesses were determined using a microscope (Jena).

The fiber batches that were manufactured are listed in Table 6B.

TABLE 6B

| Variant | Skin thickness [μm] | Skin material (placebo) | Intermediate layer thickness [μm] | Intermediate material | Core material |
|---|---|---|---|---|---|
| D1 | 100 | EVA 28 | 600 | J | M |
| D2 | 50 | EVA 28 | 600 | J | M |
| D3 | 50 | EVA 28 | 300 | J | M |
| F1 | 100 | EVA 15 | 500 | K | M |
| F2 | 100 | EVA 15 | 250 | K | M |

TABLE 6B-continued

| Variant | Skin thickness [μm] | Skin material (placebo) | Intermediate layer thickness [μm] | Intermediate material | Core material |
|---|---|---|---|---|---|
| F3 | 50 | EVA 15 | 250 | K | M |
| G1 | 300 | EVA 15 | 600 | L | M |
| G2 | 300 | EVA 15 | 200 | L | M |
| G3 | 150 | EVA 15 | 200 | L | M |

Cutting and Assembly

The three-layered fiber batches were cut into pieces of 157 mm after which they were welded with flash free welding machines at a welding temperature of 125° C.

Example 5

In-Vitro Release Rates

The in vitro release rates from the obtained vaginal rings was determined in 0.45% SLS. In tables 7A-7C the average in vitro release of the batches D-G is listed.

TABLE 7A

| | Drosperinone release [mg/day] | | | Estradiol (E2) release [mg/day] | | |
|---|---|---|---|---|---|---|
| Batch: | Day 1 | Average day (2-28) | Day 28 | Day 1 | Average day (2-28) | Day 28 |
| D1 | 1.73 | 0.943 | 0.740 | 0.402 | 0.124 | 0.103 |
| D2 | 2.94 | 1.24 | 0.880 | 0.470 | 0.133 | 0.113 |
| D3 | 2.99 | 1.23 | 0.870 | 1.078 | 0.238 | 0.211 |

Figure 17:
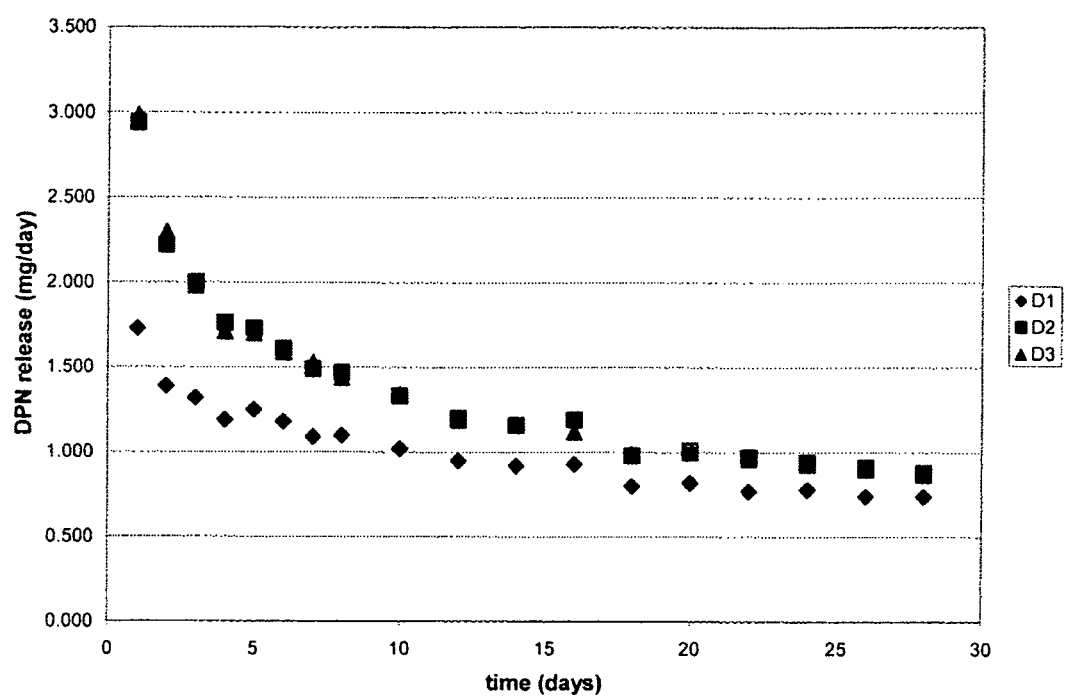
FIG. 17 shows the in-vitro Drosperinone (DPN) release profiles of ring designs of variant D1-D3.
Figure 18:
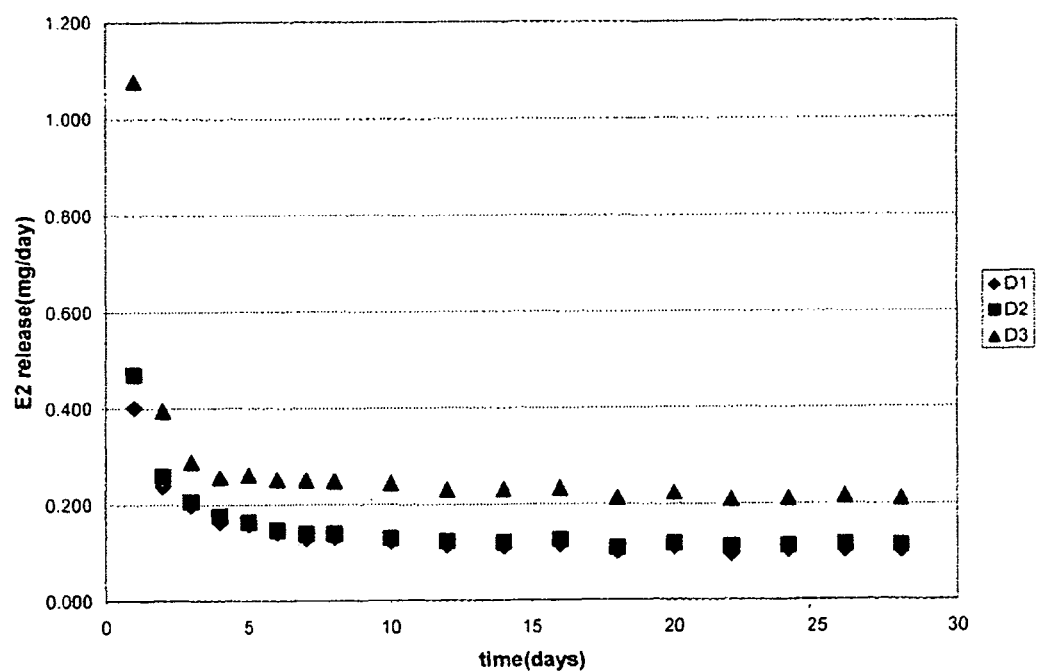
FIG. 18 shows the in-vitro Estradiol (E2) release profiles of ring designs of variant D1-D3.

The ring designs of Batch D represent formulations wherein DPN and E2 crystals are physically/spatially separated and are present in two distinct layers. The in vitro release results (FIGS. 17 and 18) of D1 and D2 show that the DPN release can be increased, while the E2 release remains largely unaffected. Comparison of D2 and D3 shows the opposite behavior, The DPN release remains unaffected while the E2 release is increased. This shows that by physical separation of the two active compounds the release rate of both compounds can be adjusted independently.

TABLE 7B

| | Levonogestrel release [mg/day] | | | Estradiol (E2) release [mg/day] | | |
|---|---|---|---|---|---|---|
| Batch: | Day 1 | Average day (2-28) | Day 28 | Day 1 | Average day (2-28) | Day 28 |
| F1 | 0.107 | 0.070 | 0.067 | 0.177 | 0.093 | 0.082 |
| F2 | 0.107 | 0.070 | 0.065 | 0.355 | 0.126 | 0.110 |
| F3 | 0.223 | 0.138 | 0.124 | 0.586 | 0.176 | 0.152 |

Figure 19:
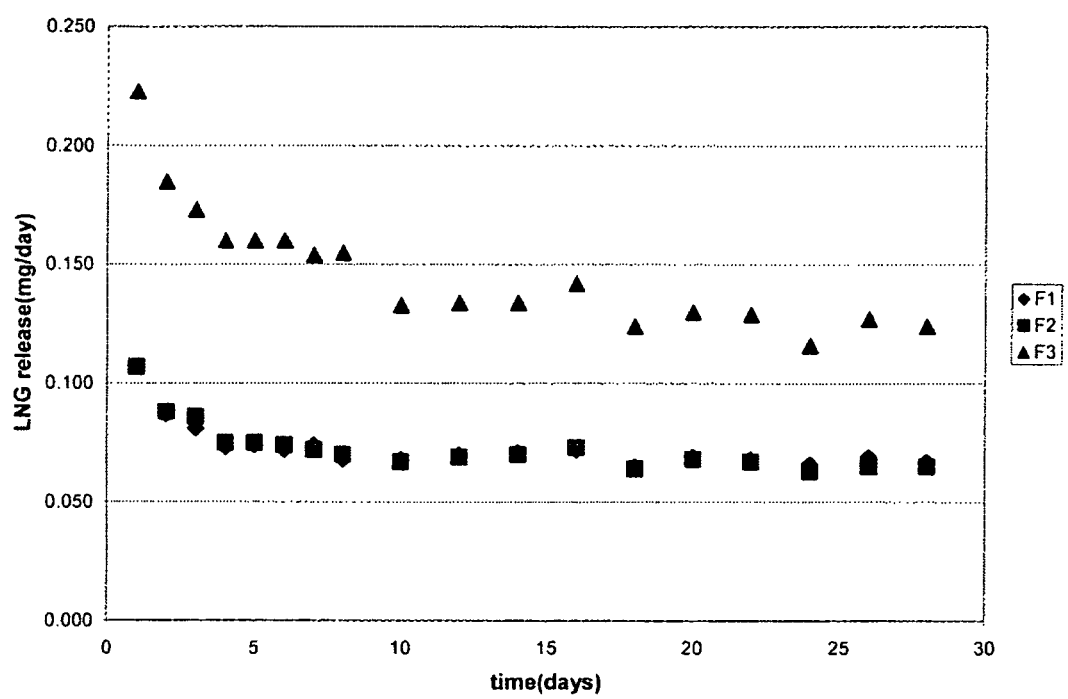
FIG. 19 shows the in-vitro Levonogestrel (LNG) release profiles of ring designs of variant F1-F3.
Figure 20:
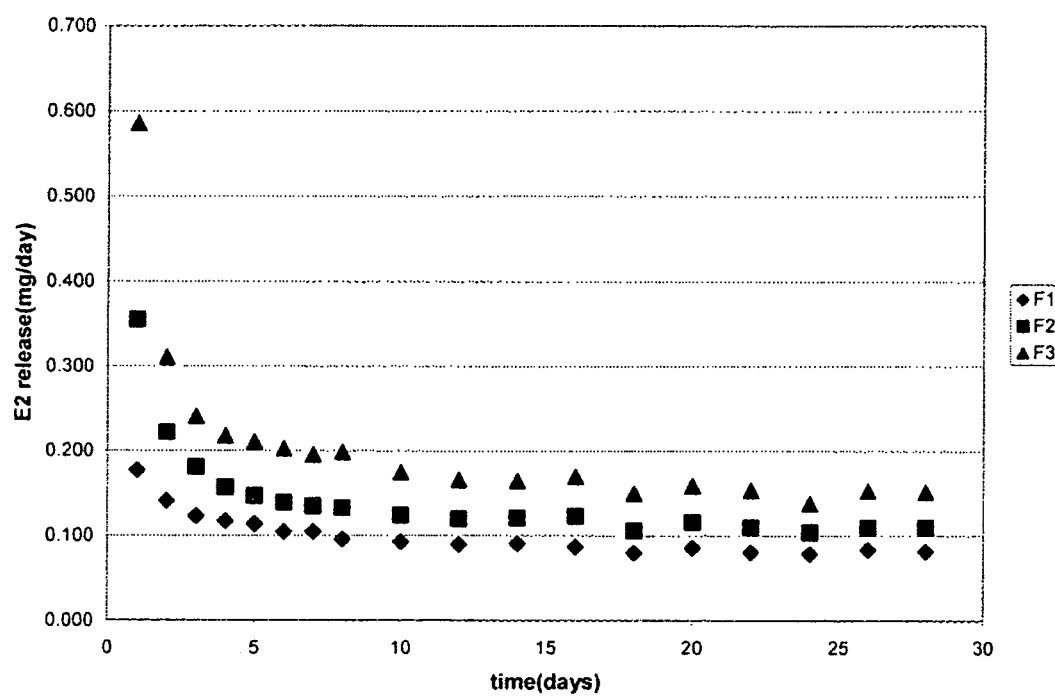
FIG. 20 shows the in-vitro Estradiol (E2) release profiles of ring designs of variant F1-F3.
Figure 21:
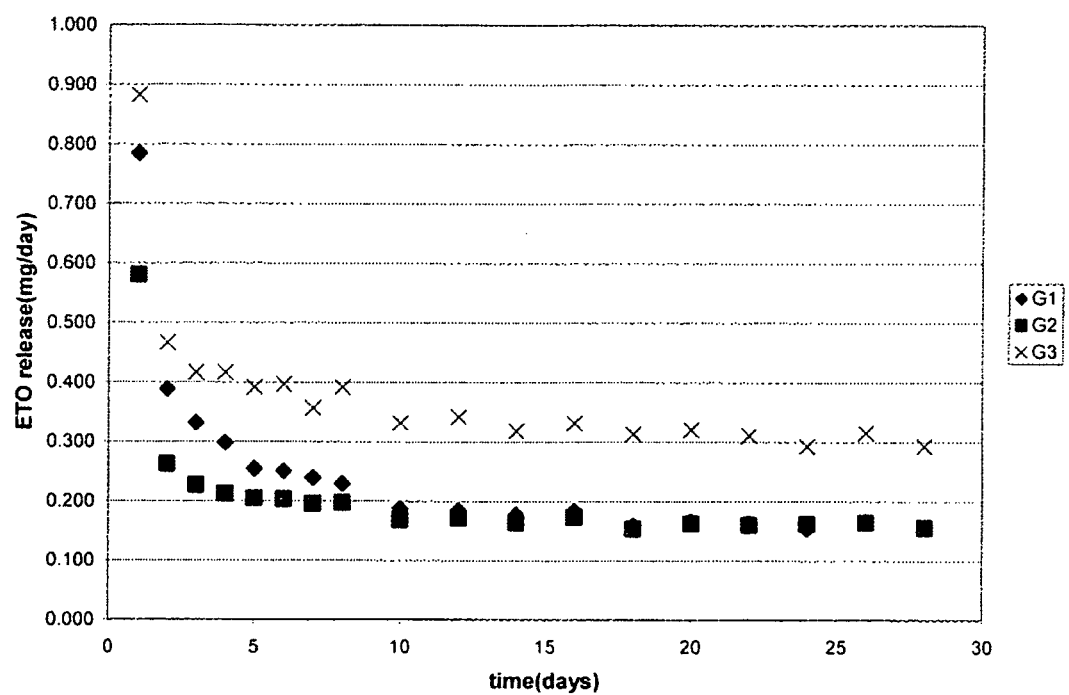
FIG. 21 shows the in-vitro Etonogestrel (ETO) release profiles of ring designs of variant G1-G3.
Figure 22:
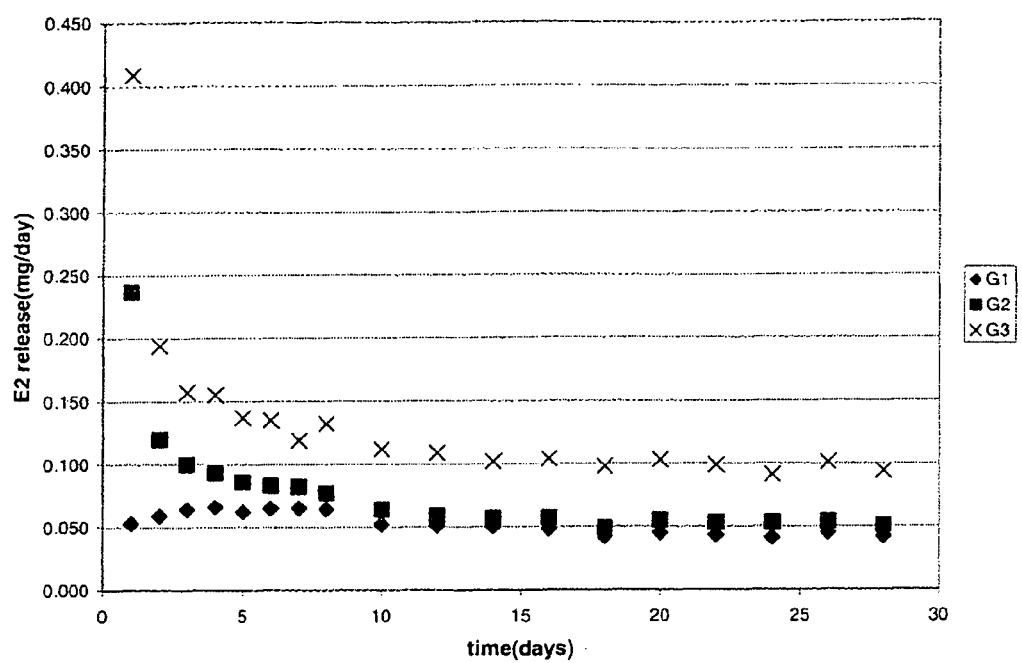
FIG. 22 shows the in-vitro Estradiol (E2) release profiles of ring designs of variant G1-G3.

The ring designs of Batch F represent formulations wherein LNG and E2 crystals are physically/spatially separated and are present in two distinct layers. The in vitro release results (FIGS. 19 and 20) of F1 and F2 show that the E2 release can be increased by decreasing the thickness of the intermediate layer, while the LNG release remains unaffected. F3 shows that the LNG release can be increased by decreasing the skin thickness.

TABLE 7C

| | Etonogestrel release [mg/day] | | | Estradiol (E2) release [mg/day] | | |
|---|---|---|---|---|---|---|
| Batch: | Day 1 | Average day (2-28) | Day 28 | Day 1 | Average day (2-28) | Day 28 |
| G1 | 0.785 | 0.200 | 0.157 | 0.053 | 0.050 | 0.042 |
| G2 | 0.581 | 0.177 | 0.156 | 0.237 | 0.064 | 0.051 |
| G3 | 0.883 | 0.340 | 0.293 | 0.409 | 0.113 | 0.094 |

The ring designs of Batch G represent formulations wherein ETO and E2 crystals are physically/spatially separated and are present in two distinct layers.

Release Ratio

Tables 8A-8C show that the present invention allows for a wide variety of release ratios.

TABLE 8A

| Batch | Average DPN day 2-28 release [mg/day] | Average E2 day 2-28 release [mg/day] | Ratio between DPN and E2 (day 2-28 release) |
|---|---|---|---|
| D1 | 0.943 | 0.124 | 7.60 |
| D2 | 1.24 | 0.133 | 9.32 |
| D3 | 1.23 | 0.238 | 5.17 |

TABLE 8B

| Batch | Average LNG day 2-28 release [mg/day] | Average E2 day 2-28 release [mg/day] | Ratio between LNG and E2 (day 2-28 release) |
|---|---|---|---|
| F1 | 0.070 | 0.093 | 0.75 |
| F2 | 0.070 | 0.126 | 0.56 |
| F3 | 0.138 | 0.176 | 0.78 |

TABLE 8C

| Batch | Average ETO day 2-28 release [mg/day] | Average E2 day 2-28 release [mg/day] | Ratio between ETO and E2 (day 2-28 release) |
|---|---|---|---|
| G1 | 0.200 | 0.050 | 4.00 |
| G2 | 0.177 | 0.064 | 2.77 |
| G3 | 0.340 | 0.113 | 3.01 |

Example 6

Four-Layered Fiber with Non-Medicated Core

The fiber can consist of three layers but may also comprise one or more additional layers. An example of an additional layer can be an unmedicated core that is covered by the medicated core layer. An unmedicated core can be advantageous for the efficiency of the drug delivery system. The core mainly acts to give the fiber its predetermined thickness, which means that the core comprises a large volume. A large core reservoir (in a three-layer design) should contain the drug substance in such a level that crystalline material is and remains present. This could means that a large excess of drug substance is needed. In case an additional non-medicated core (fourth layer) is present, the inner medicated layer must contain the drug substance at a higher concentration, without effecting the release rates. Due to this higher concentration, the average diffusion path is shorter and the release rate might be even more constant. A higher drug substance efficiency can thus be achieved without influencing the release profiles significantly. This is shown by the release profile of a ring made of a four-layered fiber which is the same as the release profile of the three-layered fiber.

Example 7

Use of the Invention for Non-Steroid Active Compounds

Figure 23:
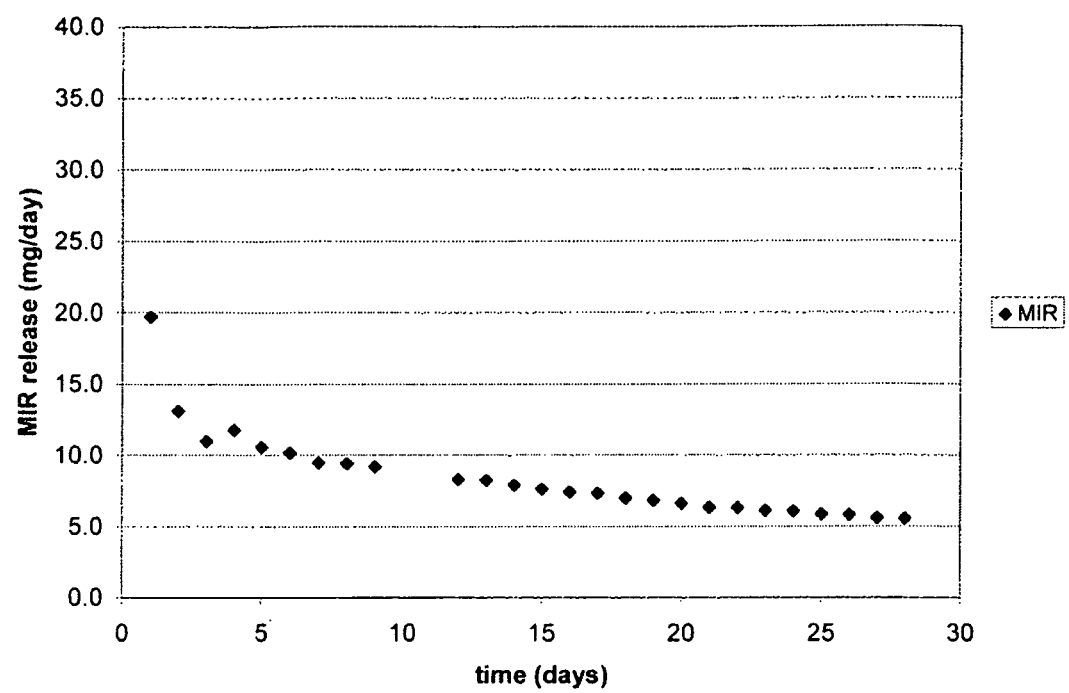
FIG. 23 shows the in-vitro Mirtazapine release profile from a three-layered ring device containing also Risperidone
Figure 24:
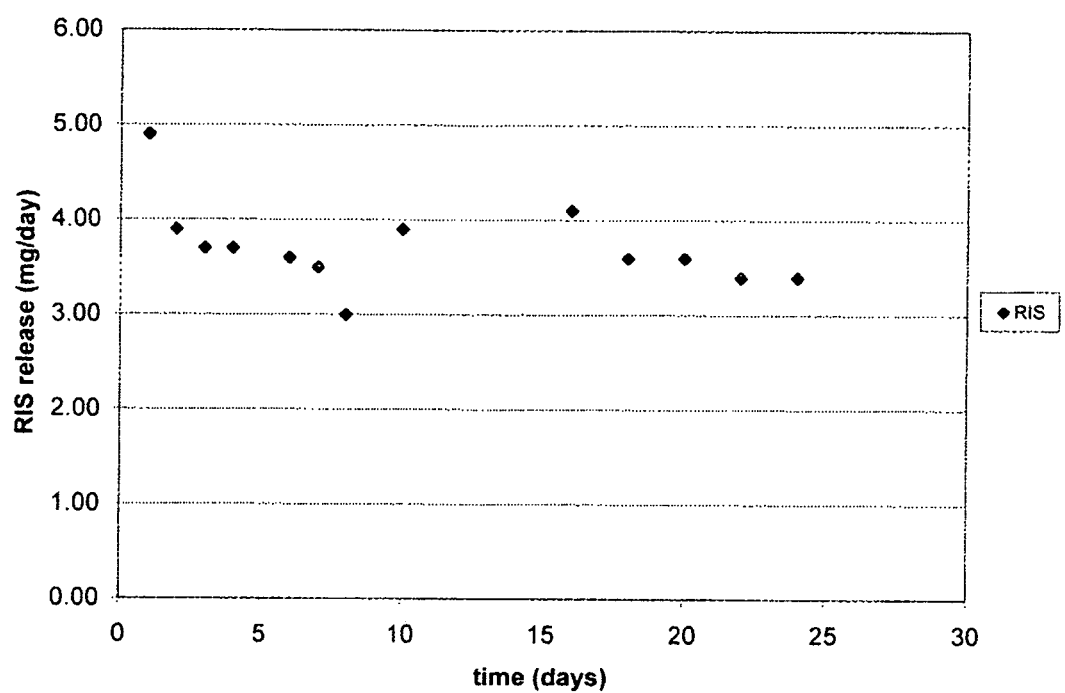
FIG. 24 shows the in-vitro Risperidone release profile from a three-layered ring device containing also Mirtazapine
Figure 25:
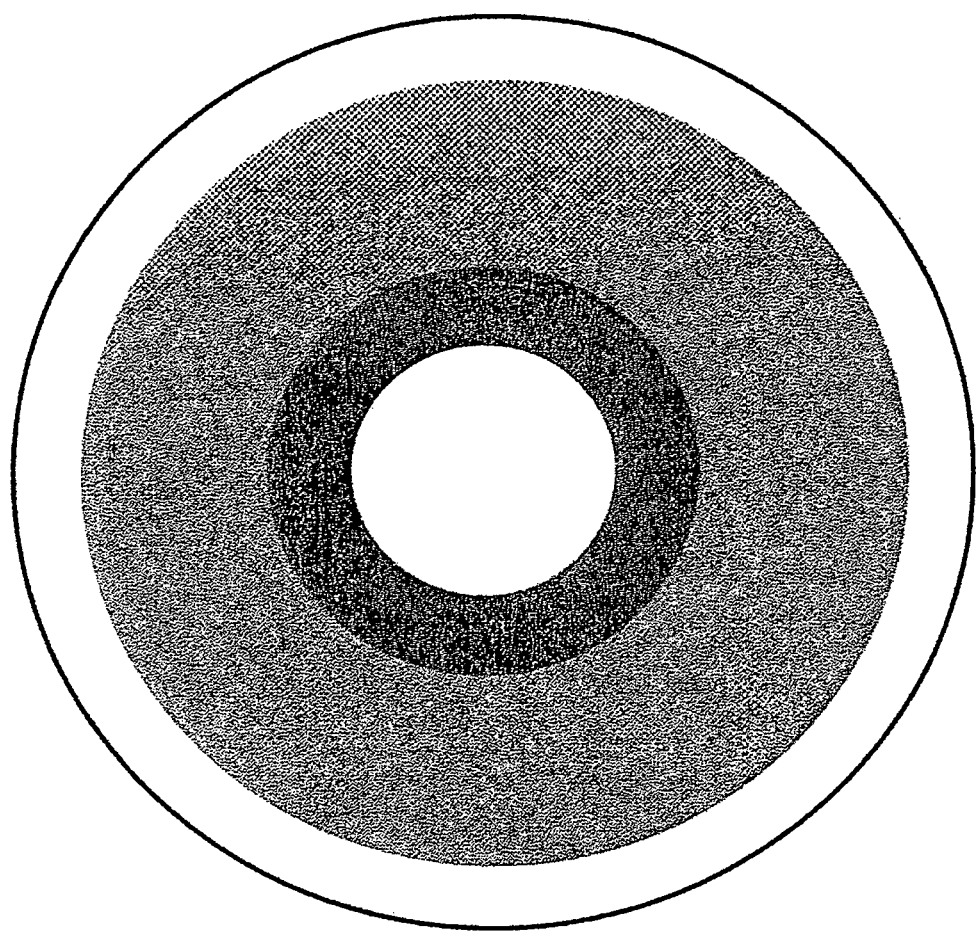
FIG. 25 shows a system comprising a non-medicated core layer (white) covered by a drug loaded core-layer (dark grey), a drug-loaded intermediate layer (light grey) and a non-medicated skin (white).
Figure 26:
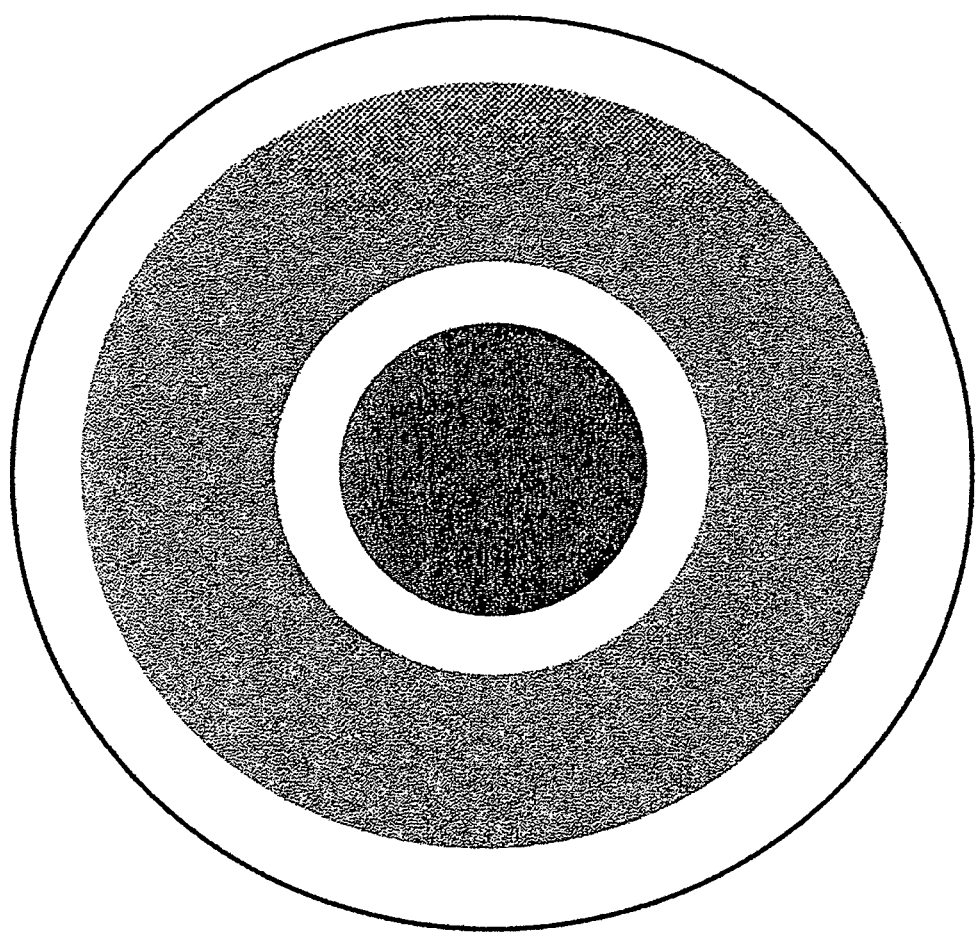
FIG. 26 shows a system comprising of a drug-loaded core layer (dark grey), a non-medicated intermediate layer (white), a drug-loaded intermediate layer (light grey) and a non-medicated skin (white).

The present invention is not limited to the use of steroids. FIG. 23 and FIG. 24 respectively show the release of Mirtazapine (MIR) and Risperidone (RIS) from a three-layered controlled release device with an EVA 33 skin thickness of 50 µm with an EVA 33 intermediate layer of 150 µm containing 60% Risperidone and an EVA 33 core containing 60% Mirtazapine. The ratio and the amount of the release rates of Mirtazapine and Risperidone can be tuned independently by adjusting the different layer materials and thicknesses.

The invention claimed is:

1. A drug delivery system comprising at least one compartment, which comprises (i) a drugloaded thermoplastic polymer core layer, (ii) a drug-loaded thermoplastic polymer intermediate layer and (iii) a non-medicated thermoplastic polymer skin covering the intermediate layer, wherein the core layer is loaded with crystals of a first compound, and wherein the intermediate layer is loaded with crystals of a second compound, wherein the first compound or second compound is nomegestrol acetate (NOMAc) and wherein the remnant content of the nomegestrol acetate after 21-31 days of use of the drug delivery system is equal to or less than 40% by weight.

2. The drug delivery system according to claim 1, wherein the core layer forms the core of the drug delivery system.

3. The drug delivery system according to claim 1, wherein an additional non-medicated core is covered by the core layer.

4. The drug delivery system according to claim 1, wherein an additional non-medicated intermediate layer is between the core layer and the drug-loaded intermediate layer.

5. The drug delivery system according to claim 1, wherein the delivery system has the form of a ring, an implant, an intrauterine system (IUS), a helical coil or a spring.

6. The drug delivery system according to claim 5, wherein the delivery system has a substantially ring-shaped form and is intended for vaginal administration.

7. The drug delivery system according to claim 1, wherein the first compound is nomegestrol acetate (NOMAc) and the second compound is an estrogen.

8. The drug delivery system according to claim 1, wherein the first compound is an estrogen and the second compound is nomegestrol acetate (NOMAc).

9. The drug delivery system according to claim 7, wherein the estrogen is selected from the group consisting of estradiol, ethinyl estradiol, estriol, estetrol, esters thereof, pseudopolymorphs thereof, pharmaceutically acceptable solvates thereof, hydrates thereof, hemihydrates thereof and any other suitable steroidal compound with estrogenic activity.

10. The drug delivery system according to claim 9, wherein the estrogen is estradiol or estradiol hemihydrate.

11. The drug delivery system according to claim 8, wherein the estrogen is selected from the group consisting of estradiol, ethinyl estradiol, estriol, estetrol, esters thereof, pseudopolymorphs thereof, pharmaceutically acceptable solvates thereof, hydrates thereof, hemihydrates thereof and any other suitable steroidal compound with estrogenic activity.

12. A drug delivery system according to claim 1, wherein at least the skin but optionally also the core layer and the intermediate layer comprise ethylene-vinyl acetate copolymer as the thermoplastic polymer.

13. A drug delivery system according to claim 12, wherein the core layer and the intermediate layer comprise the same grade of ethylene-vinyl acetate copolymer.

14. A drug delivery system according to claim 12, wherein the core and the intermediate layer comprise a different grade of ethylene-vinyl acetate copolymer.

15. A drug delivery system according to claim 7, wherein nomegestrol acetate is present at about 5-35% by weight.

16. A drug delivery system according to claim 7, wherein nomegestrol acetate is present at about 35% by weight.

17. A drug delivery system according to claim 8, wherein the estrogen is present at about 3-70% by weight.

18. A drug delivery system according to claim 17, wherein the estrogen is estradiol or estradiol hemihydrate.

19. A drug delivery system according to claim 7, wherein the estradiol is present at about 3-27% by weight.

20. A drug delivery system according to claim 19, wherein the estradiol is present at about 9-27% by weight.

21. A drug delivery system according to claim 17, wherein the estradiol is present at about 3-20% by weight.

22. A drug delivery system according to claim 21, wherein the estradiol is present at about 4.5-9% by weight.

23. A drug delivery system according to claim 8, wherein the nomegestrol acetate is present at about 10-70% by weight.

24. A drug delivery system according to claim 8, wherein the nomegestrol acetate is present at about 20-60% by weight.

25. A drug delivery system according to claim 24, wherein the nomegestrol acetate is present at about 35-60% by weight.

26. A drug delivery system according to claim 1, wherein the intermediate layer additionally contains an anti-microbial agent.

27. A drug delivery system according to claim 1, wherein the core additionally contains an anti-microbial agent.

28. A drug delivery system according to claim 1, wherein the device contains two compartments.

29. A drug delivery system according to claim 28, wherein the second compartment contains an anti-microbial agent.

30. A method of contraception which comprises the steps of (i) positioning the drug delivery system of claim 1 within the female vaginal tract and (ii) retaining the system within the vaginal tract for prolonged period of time.

31. The method of claim 30, wherein the prolonged period of time is about 21 days.

32. The method of claim 30, wherein the prolonged period of time is about 24 days.

33. A method of contraception which comprises the steps of (i) positioning the drug delivery system of claim 1 within the female vaginal tract (ii) retaining the system within the vaginal tract for at least about 21 days and (iii) removing the system for an approximate one week period to permit menstruation.

34. A method of contraception which comprises the steps of (i) positioning the drug delivery system of claim 1 within the female vaginal tract (ii) retaining the system within the vaginal tract for at least about 24 days and (iii) removing the system for an approximate 4 day period to permit menstruation.

* * * * *